United States Patent
Gray et al.

(10) Patent No.: US 11,279,707 B2
(45) Date of Patent: Mar. 22, 2022

(54) NEK INHIBITORS AND METHODS OF USE

(71) Applicant: DANA-FARBER CANCER INSTITUTE, INC., Boston, MA (US)

(72) Inventors: Nathanael S. Gray, Boston, MA (US); Quan Cai, Brookline, MA (US); Tinghu Zhang, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/956,048

(22) PCT Filed: Dec. 21, 2018

(86) PCT No.: PCT/US2018/067188
§ 371 (c)(1),
(2) Date: Jun. 19, 2020

(87) PCT Pub. No.: WO2019/126696
PCT Pub. Date: Jun. 27, 2019

(65) Prior Publication Data
US 2020/0361948 A1    Nov. 19, 2020

Related U.S. Application Data

(60) Provisional application No. 62/609,634, filed on Dec. 22, 2017.

(51) Int. Cl.
*C07D 487/14* (2006.01)
(52) U.S. Cl.
CPC ................ *C07D 487/14* (2013.01)

(58) Field of Classification Search
CPC .................................................. C07D 487/14
USPC ........................................................ 514/250
See application file for complete search history.

(56) References Cited

FOREIGN PATENT DOCUMENTS

| WO | 2004076454 A1 | 9/2004 |
| WO | 2006089298 A2 | 8/2006 |
| WO | 2013071217 A1 | 5/2013 |
| WO | 2014145909 A2 | 9/2014 |
| WO | 2018075608 A1 | 4/2018 |

OTHER PUBLICATIONS

PCT Application No. PCT/US2018/067188, International Preliminary Report on Patentability, dated Jun. 23, 2020, eight pages.
Xi Jian Bei et al., "Structure-Based Design and Synthesis of Imidazo[1,2-a]pyridine Derivatives as novel and Potent Nek2 Inhibitors within Vitroandin Vivoantitumor Activities", European Journal of Medicinal Chemistry, Elsevier, Amsterdam, NL, vol. 126, Dec. 12, 2016, pp. 1083-1106.
Coxon, Christopher R. et al., "Structure-guided Design of Purine-Based Probes for selective Nek2 Inhibition", Oncotarget, vol. 8, No. 12, Mar. 21, 2017, pp. 19089-19124.

*Primary Examiner* — Taofiq A Solola
(74) *Attorney, Agent, or Firm* — Lathrop GPM LLP; Brian C. Trinque; Nicole Sassu

(57) ABSTRACT

Compounds of the present application or pharmaceutically acceptable salts thereof are provided and methods involving compounds of the present application as effective inhibitors of NEK are also provided.

23 Claims, No Drawings

NEK INHIBITORS AND METHODS OF USE

RELATED APPLICATION

This application claims priority to and the benefit of U.S. Appl. No. 62/609,634, filed on Dec. 22, 2017, the entire contents of which are incorporated herein by reference.

BACKGROUND

The NEK serine/threonine kinase family contains 11 kinases: NEK1 to NEK11. NEK has been recognized as cell cycle regulator protein and is essential for mitosis. NEK2, NEK6, NEK7, and NEK9 contribute to the establishment of the microtubule-based mitotic spindle, whereas NEK1, NEK10, and NEK11 are implicated in the DNA damage response. NEK1 and NEK8 also function within cilia, the microtubule-based structures that are nucleated from basal bodies.

Upregulation of the NEK family proteins has been found in various cancer cell lines and tumors. Recent emergence of comprehensive cancer genomes also highlights certain members of the NEK family as targets of frequent mutations. Targeting cell cycle regulator proteins, such as CDK, Aurora, and PIK1, for cancer has been pursed with a large number of small molecules in the clinic development stage. Thus, modulation of the NEK kinase activity with small molecule compounds provides a new therapeutic avenue for the treatment and/or prevention of various diseases, such as cancer, where deregulation of NEK is involved. Accordingly, compounds with improved properties to modulate NEK are needed. The present application addresses the need.

SUMMARY

In one aspect, the present application relates to a compound of Formula I:

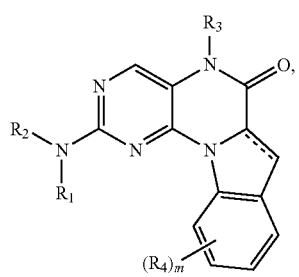

or a pharmaceutically acceptable salt thereof, wherein $R_1$, $R_2$, $R_3$, $R_4$, and m are each defined herein.

In another aspect, the present application relates to a pharmaceutical composition comprising a therapeutically effective amount of a compound of the application or a pharmaceutically acceptable salt thereof, and a pharmaceutically acceptable carrier.

Another aspect of the present application relates to a method of modulating (e.g., inhibiting) NEK. The method comprises administering to a subject in need thereof a therapeutically effective amount of a compound of the application or a pharmaceutically acceptable salt thereof, or a pharmaceutical composition of the application.

Another aspect of the present application relates to a method of treating or preventing a disease (e.g., a disease in which NEK plays a role). The method comprises administering to a subject in need thereof a therapeutically effective amount of a compound of the application or a pharmaceutically acceptable salt thereof, or a pharmaceutical composition of the application. In one aspect, the disease is a NEK mediated disorder. In one aspect, the disease is a proliferative disease (e.g., a proliferative disease in which NEK plays a role).

Another aspect of the present application relates to a method of treating or preventing cancer in a subject, wherein the cell of the cancer comprises an activated NEK or wherein the subject is identified as being in need of inhibition of NEK for the treatment or prevention of cancer. The method comprises administering to the subject a therapeutically effective amount of a compound of the application or a pharmaceutically acceptable salt thereof, or a pharmaceutical composition of the application.

Another aspect of the present application relates to a kit comprising a compound of the application or a pharmaceutically acceptable salt thereof, or a pharmaceutical composition of the application.

Another aspect of the present application relates to a compound of the application or a pharmaceutically acceptable salt thereof, or a pharmaceutical composition of the application, for use in the manufacture of a medicament for modulating (e.g., inhibiting) NEK, for treating or preventing a disease (e.g., a disease in which NEK plays a role), or for treating or preventing cancer in a subject, wherein the cell of the cancer comprises an activated NEK or wherein the subject is identified as being in need of inhibition of NEK for the treatment or prevention of cancer.

Another aspect of the present application relates to use of a compound of the application or a pharmaceutically acceptable salt thereof, or a pharmaceutical composition of the application, in the manufacture of a medicament for modulating (e.g., inhibiting) NEK, for treating or preventing a disease (e.g., a disease in which NEK plays a role), or for treating or preventing cancer in a subject, wherein the cell of the cancer comprises an activated NEK or wherein the subject is identified as being in need of inhibition of NEK for the treatment or prevention of cancer.

Another aspect of the present application relates to a compound of the application or a pharmaceutically acceptable salt thereof, or a pharmaceutical composition of the application, for use in modulating (e.g., inhibiting) NEK, in treating or preventing a disease (e.g., a disease in which NEK plays a role), or in treating or preventing cancer in a subject, wherein the cell of the cancer comprises an activated NEK or wherein the subject is identified as being in need of inhibition of NEK for the treatment or prevention of cancer.

Another aspect of the present application relates to use of a compound of the application or a pharmaceutically acceptable salt thereof, or a pharmaceutical composition of the application, in modulating (e.g., inhibiting) NEK, in treating or preventing a disease (e.g., a disease in which NEK plays a role), or in treating or preventing cancer in a subject, wherein the cell of the cancer comprises an activated NEK or wherein the subject is identified as being in need of inhibition of NEK for the treatment or prevention of cancer.

The present application provides inhibitors of NEK that are therapeutic agents in the treatment or prevention of diseases such as cancer and metastasis.

The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The contents of all references (including literature references, issued patents, published patent applications, and co-pending patent applications) cited throughout this application are hereby expressly incorporated herein in their entireties by reference. The references cited herein are not admitted to be prior art to the application.

DETAILED DESCRIPTION

The present application relates to compounds that are shown to potently and selectively inhibit NEK. In one embodiment, a compound of the present application is represented by Formula I:

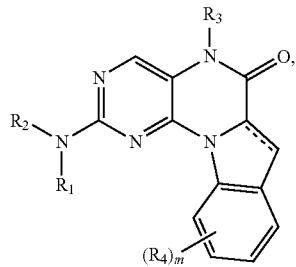

(I)

or a pharmaceutically acceptable salt thereof, wherein:

represents a single or double bond;

$R_1$ is $C_3$-$C_8$ cycloalkyl, heterocyclyl comprising one or two 5- or 6-membered rings and 1-4 heteroatoms selected from N, O, and S, $C_6$-$C_{10}$ aryl, or heteroaryl comprising one or two 5- or 6-membered rings and 1-4 heteroatoms selected from N, O, and S, wherein the cycloalkyl, heterocyclyl, aryl, or heteroaryl is substituted with one or more $R_{S1}$;

each $R_{S1}$ independently is $C_1$-$C_6$ alkyl, $C_1$-$C_6$ haloalkyl, halogen, cyano, $OR_a$, $NR_aR_b$, $C(O)NR_aR_b$, $S(O)_2NR_aR_b$, or L-$T_1$, wherein at least one $R_{S1}$ is $C_1$-$C_6$ haloalkyl, $S(O)_2NR_aR_b$, or L-$T_1$;

L is a bond, —C(O)—, —S(O)$_n$—, —S(O)$_n$NH—, —C(O)NH—, or —(CH$_2$)$_p$—;

$T_1$ is $C_3$-$C_8$ cycloalkyl or heterocyclyl comprising one 5- or 6-membered ring and 1-4 heteroatoms selected from N, O, and S, wherein the cycloalkyl or heterocyclyl is optionally substituted with one or more $X_1$;

each $X_1$ independently is $C_1$-$C_6$ alkyl, $C_1$-$C_6$ haloalkyl, halogen, cyano, $C_3$-$C_8$ cycloalkyl, $C_6$-$C_{10}$ aryl, heterocyclyl comprising one or two 5- or 6-membered rings and 1-4 heteroatoms selected from N, O, and S, heteroaryl comprising one or two 5- or 6-membered rings and 1-4 heteroatoms selected from N, O, and S, $OR_a$, $NR_aR_b$, $C(O)OR_a$, $C(O)NR_aR_b$, $S(O)_nOR_a$, or $S(O)_nNR_aR_b$, wherein the cycloalkyl, aryl, heterocyclyl, or heteroaryl is optionally substituted with one or more $R_{S2}$;

each $R_{S2}$ independently is $C_1$-$C_6$ alkyl, $C_1$-$C_6$ haloalkyl, halogen, cyano, $OR_a$, or $NR_aR_b$, $R_2$ is H or $C_1$-$C_6$ alkyl;

$R_3$ is $C_1$-$C_6$ alkyl;

each $R_4$ independently is $C_1$-$C_6$ alkyl, $C_1$-$C_6$ haloalkyl, halogen, cyano, $OR_a$, or $NR_aR_b$;

each $R_a$ and each $R_b$ independently is H or $C_1$-$C_6$ alkyl;

m is 0, 1, 2, 3, or 4;

each n independently is 0, 1, or 2; and p is 1, 2, 3, 4, 5, or 6.

In one embodiment, a compound of Formula I is of Formula Ia1 or Ia2:

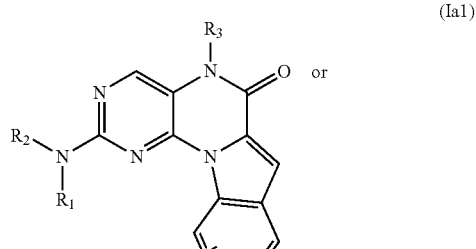

(Ia1)

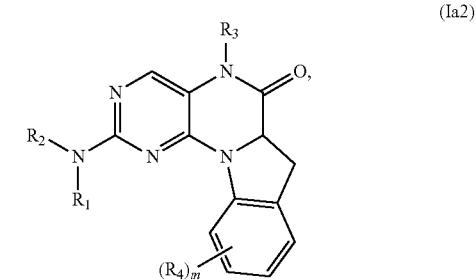

(Ia2)

or a pharmaceutically acceptable salt thereof, wherein $R_1$, $R_2$, $R_3$, $R_4$, $R_{S1}$, $R_{S2}$, $R_a$, $R_b$, $T_1$, $X_1$, L, m, n, and p are each as defined in Formula I.

For a compound of Formula I, Ia1, or Ia2:

In one embodiment, $R_1$ is $C_6$-$C_{10}$ aryl or heteroaryl comprising one or two 5- or 6-membered rings and 1-4 heteroatoms selected from N, O, and S, wherein the aryl or heteroaryl is substituted with one or more $R_{S1}$. In one embodiment, $R_1$ is $C_6$-$C_{10}$ aryl or heteroaryl comprising one 5- or 6-membered ring and 1-4 heteroatoms selected from N, O, and S, wherein the aryl or heteroaryl is substituted with one or more $R_{S1}$.

In one embodiment, $R_1$ is $C_3$-$C_8$ cycloalkyl selected from cyclopropyl, cyclobutyl, cyclopentyl, cyclohexyl, cycloheptyl, and cyclooctyl, each substituted with one or more $R_{S1}$. In one embodiment, $R_1$ is $C_3$-$C_6$ cycloalkyl selected from cyclopropyl, cyclobutyl, cyclopentyl, and cyclohexyl, each substituted with one or more $R_{S1}$. In one embodiment, $R_1$ is cyclopentyl or cyclohexyl, each substituted with one or more $R_{S1}$.

In one embodiment, $R_1$ is heterocyclyl comprising one or two 5- or 6-membered rings and 1-4 heteroatoms selected from N, O, and S, substituted with one or more $R_{S1}$. In one embodiment, $R_1$ is heterocyclyl comprising one 5- or 6-membered ring and 1-4 heteroatoms selected from N, O, and S, substituted with one or more $R_{S1}$. In one embodiment, $R_1$ is heterocyclyl comprising one 5- or 6-membered ring and 1-2 heteroatoms selected from N, O, and S, substituted with one or more $R_{S1}$.

In one embodiment, $R_1$ is $C_6$-$C_{10}$ aryl substituted with one or more $R_{S1}$. In one embodiment, $R_1$ is phenyl substituted with one or more $R_{S1}$.

In one embodiment, $R_1$ is heteroaryl comprising one or two 5- or 6-membered rings and 1-4 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, quinoxalinyl, benzimidazolyl, or benzooxazolyl), substituted with one or more $R_{S1}$. In one embodiment, $R_1$ is heteroaryl comprising one 5- or 6-membered ring and 1-4 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, or furanyl), substituted with one or more $R_{S1}$. In one embodiment, $R_1$ is heteroaryl comprising one 5- or 6-membered ring and 1-2 heteroatoms selected from N, O, and S, substituted with one or more $R_{S1}$. In one embodiment, $R_1$ is pyridinyl, pyrazolyl, or imidazolyl, each substituted with one or more $R_{S1}$.

In one embodiment, $R_1$ is substituted with one $R_{S1}$.

In one embodiment, $R_1$ is substituted with two $R_{S1}$.

In one embodiment, each $R_{S1}$ independently is $C_1$-$C_6$ alkyl (e.g., methyl, ethyl, n-propyl, i-propyl, n-butyl, i-butyl, s-butyl, t-butyl, pentyl, or hexyl), $C_1$-$C_6$ haloalkyl (e.g., methyl, ethyl, n-propyl, i-propyl, n-butyl, i-butyl, s-butyl, t-butyl, pentyl, or hexyl, each substituted with one or more halogen (e.g., F, Cl, Br, or I)), halogen (e.g., F, Cl, Br, or I), cyano, $OR_a$, $NR_aR_b$, $C(O)NR_aR_b$, $S(O)_2NR_aR_b$, or L-$T_1$, wherein at least one $R_{S1}$ is L-$T_1$.

In one embodiment, one $R_{S1}$ is L-$T_1$.

In one embodiment, one $R_{S1}$ is L-$T_1$; and at least one $R_{S1}$ is $C_1$-$C_6$ alkyl (e.g., methyl, ethyl, n-propyl, i-propyl, n-butyl, i-butyl, s-butyl, t-butyl, pentyl, or hexyl), $C_1$-$C_6$ haloalkyl (e.g., methyl, ethyl, n-propyl, i-propyl, n-butyl, i-butyl, s-butyl, t-butyl, pentyl, or hexyl, each substituted with one or more halogen (e.g., F, Cl, Br, or I)), halogen (e.g., F, Cl, Br, or I), cyano, $OR_a$, $NR_aR_b$, $C(O)NR_aR_b$, or $S(O)_2NR_aR_b$. In one embodiment, one $R_{S1}$ is L-$T_1$; and at least one $R_{S1}$ is $C_1$-$C_6$ alkyl (e.g., methyl, ethyl, n-propyl, i-propyl, n-butyl, i-butyl, s-butyl, t-butyl, pentyl, or hexyl), $C_1$-$C_6$ haloalkyl (e.g., methyl, ethyl, n-propyl, i-propyl, n-butyl, i-butyl, s-butyl, t-butyl, pentyl, or hexyl, each substituted with one or more halogen (e.g., F, Cl, Br, or I)), halogen (e.g., F, Cl, Br, or I), cyano, or $OR_a$. In one embodiment, one $R_{S1}$ is L-$T_1$; and at least one $R_{S1}$ is methyl, $CF_3$, F, Cl, or $OR_a$.

In one embodiment, two $R_{S1}$ are L-$T_1$.

In one embodiment, one $R_{S1}$ is $C_1$-$C_6$ haloalkyl (e.g., methyl, ethyl, n-propyl, i-propyl, n-butyl, i-butyl, s-butyl, 1-butyl, pentyl, or hexyl, each substituted with one or more halogen (e.g., F, Cl, Br, or I)).

In one embodiment, one $R_{S1}$ is $S(O)_2NR_aR_b$.

In one embodiment, L is a bond, —C(O)—, or —(CH$_2$)$_p$—. In one embodiment, L is a bond.

In one embodiment, L is —C(O)—. In one embodiment, L is —(CH$_2$)$_p$—.

In one embodiment, L is —S(O)$_n$—, —S(O)$_n$NH—, or —C(O)NH—.

In one embodiment, $T_1$ is $C_3$-$C_8$ cycloalkyl selected from cyclopropyl, cyclobutyl, cyclopentyl, cyclohexyl, cycloheptyl, and cyclooctyl, each optionally substituted with one or more $X_1$. In one embodiment, $T_1$ is $C_3$-$C_6$ cycloalkyl selected from cyclopropyl, cyclobutyl, cyclopentyl, and cyclohexyl, each optionally substituted with one or more $X_1$. In one embodiment, $T_1$ is cyclopentyl or cyclohexyl, each optionally substituted with one or more $X_1$.

In one embodiment, $T_1$ is heterocyclyl comprising one 5- or 6-membered ring and 1-4 heteroatoms selected from N, O, and S (e.g., pyrrolidinyl, pyrazolinyl, pyrazolidinyl, imidazolinyl, imidazolidinyl, piperidinyl, piperazinyl, or morpholinyl), optionally substituted with one or more $X_1$. In one embodiment, $T_1$ is heterocyclyl comprising one 6-membered ring and 1-4 heteroatoms selected from N, O, and S (e.g., piperidinyl, piperazinyl, or morpholinyl), optionally substituted with one or more $X_1$.

In one embodiment, each $X_1$ independently is $C_1$-$C_6$ alkyl (e.g., methyl, ethyl, n-propyl, i-propyl, n-butyl, i-butyl, s-butyl, t-butyl, pentyl, or hexyl), $C_1$-$C_6$ haloalkyl (e.g., methyl, ethyl, n-propyl, i-propyl, n-butyl, i-butyl, s-butyl, t-butyl, pentyl, or hexyl, each substituted with one or more halogen (e.g., F, Cl, Br, or I)), halogen (e.g., F, Cl, Br, or I), cyano, $C_3$-$C_8$ cycloalkyl (e.g., cyclopropyl, cyclobutyl, cyclopentyl, cyclohexyl, cycloheptyl, or cyclooctyl), $C_6$-$C_{10}$ aryl (e.g., phenyl), heterocyclyl comprising one or two 5- or 6-membered rings and 1-4 heteroatoms selected from N, O, and S (e.g., pyrrolidinyl, pyrazolinyl, pyrazolidinyl, imidazolinyl, imidazolidinyl, piperidinyl, piperazinyl, or morpholinyl), heteroaryl comprising one or two 5- or 6-membered rings and 1-4 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, or furanyl), $OR_a$, or $S(O)_nNR_aR_b$, wherein the cycloalkyl, aryl, heterocyclyl, or heteroaryl is optionally substituted with one or more $R_{S2}$. In one embodiment, each $X_1$ independently is $C_1$-$C_6$ alkyl, $C_1$-$C_6$ haloalkyl, halogen, cyano, $C_3$-$C_8$ cycloalkyl, or heterocyclyl comprising one or two 5- or 6-membered rings and 1-4 heteroatoms selected from N, O, and S, $OR_a$, $NR_aR_b$, $C(O)OR_a$, $C(O)NR_aR_b$, $S(O)_nOR_a$, or $S(O)_nNR_aR_b$, wherein the cycloalkyl or heterocyclyl is optionally substituted with one or more $R_{S2}$. In one embodiment, each $X_1$ independently is $C_1$-$C_6$ alkyl, $C_1$-$C_6$ haloalkyl, halogen, cyano, $C_3$-$C_8$ cycloalkyl, heterocyclyl comprising one or two 5- or 6-membered rings and 1-4 heteroatoms selected from N, O, and S, or $OR_a$, wherein the cycloalkyl or heterocyclyl is optionally substituted with one or more $R_{S2}$. In one embodiment, each $X_1$ independently is $C_1$-$C_6$ alkyl, $C_1$-$C_6$ haloalkyl, halogen, cyano, $C_3$-$C_8$ cycloalkyl, heterocyclyl comprising one 5- or 6-membered ring and 1-4 heteroatoms selected from N, O, and S (e.g., pyrrolidinyl, pyrazolinyl, pyrazolidinyl, imidazolinyl, imidazolidinyl, piperidinyl, piperazinyl, or morpholinyl), or $OR_a$, wherein the cycloalkyl or heterocyclyl is optionally substituted with one or more $R_{S2}$. In one embodiment, each $X_1$ independently is $C_1$-$C_6$ alkyl, $C_1$-$C_6$ haloalkyl, halogen, cyano, $C_3$-$C_8$ cycloalkyl, heterocyclyl comprising one 6-membered ring and 1-4 heteroatoms selected from N, O, and S (e.g., piperidinyl, piperazinyl, or morpholinyl), $OR_a$, or $C(O)NR_aR_b$, wherein the cycloalkyl or heterocyclyl is optionally substituted with one or more $R_{S2}$. In one embodiment, each $X_1$ independently is methyl, ethyl, $CF_3$, F, Cl, cyano, $C_3$-$C_8$ cycloalkyl, heterocyclyl comprising one 6-membered ring and 1-4 heteroatoms selected from N, O, and S (e.g., piperidinyl, piperazinyl, or morpholinyl), $OR_a$, or $C(O)NR_aR_b$, wherein the cycloalkyl or heterocyclyl is optionally substituted with one or more $R_{S2}$.

In one embodiment, each $R_{S2}$ independently is $C_1$-$C_6$ alkyl (e.g., methyl, ethyl, i-propyl, i-propyl, n-butyl, i-butyl, s-butyl, i-butyl, pentyl, or hexyl), $C_1$-$C_6$ haloalkyl (e.g., methyl, ethyl, n-propyl, i-propyl, n-butyl, i-butyl, s-butyl, t-butyl, pentyl, or hexyl, each substituted with one or more halogen (e.g., F, Cl, Br, or I)), halogen (e.g., F, Cl, Br, or I), cyano, $OR_a$, or $NR_aR_b$. In one embodiment, each $R_{S2}$ independently is $C_1$-$C_6$ alkyl, $C_1$-$C_6$ haloalkyl, or halogen. In one embodiment, each $R_{S2}$ independently is methyl, ethyl, methyl or ethyl substituted with one or more halogen, or halogen. In one embodiment, at least one $R_{S2}$ is methyl.

In one embodiment, $R_2$ is H.

In one embodiment, $R_2$ is $C_1$-$C_6$ alkyl (e.g., methyl, ethyl, ii-propyl, i-propyl, n-butyl, i-butyl, s-butyl, t-butyl, pentyl, or hexyl).

In one embodiment, $R_3$ is $C_1$-$C_6$ alkyl (e.g., methyl, ethyl, n-propyl, i-propyl, n-butyl, i-butyl, s-butyl, 1-butyl, pentyl, or hexyl). In one embodiment, $R_3$ is $C_1$-$C_3$ alkyl (e.g., methyl, ethyl, i-propyl, or i-propyl). In one embodiment, $R_3$ is methyl or ethyl.

In one embodiment, each $R_4$ independently is $C_1$-$C_6$ alkyl (e.g., methyl, ethyl, n-propyl, i-propyl, n-butyl, i-butyl, s-butyl, i-butyl, pentyl, or hexyl), $C_1$-$C_6$ haloalkyl (e.g., methyl, ethyl, n-propyl, i-propyl, n-butyl, i-butyl, s-butyl, t-butyl, pentyl, or hexyl, each substituted with one or more halogen (e.g., F, Cl, Br, or I)), halogen (e.g., F, Cl, Br, or I), cyano, $OR_a$, or $NR_aR_b$.

In one embodiment, $R_a$ is H.

In one embodiment, $R_a$ is $C_1$-$C_6$ alkyl (e.g., methyl, ethyl, n-propyl, i-propyl, n-butyl, i-butyl, s-butyl, t-butyl, pentyl, or hexyl).

In one embodiment, $R_b$ is H.

In one embodiment, $R_b$ is $C_1$-$C_6$ alkyl (e.g., methyl, ethyl, i-propyl, i-propyl, n-butyl, i-butyl, s-butyl, 1-butyl, pentyl, or hexyl).

In one embodiment, m is 0.

In one embodiment, m is 1, 2, 3, or 4.

In one embodiment, m is 0, 1, or 2.

In one embodiment, m is 1 or 2.

In one embodiment, n is 0. In one embodiment, n is 1. In one embodiment, n is 2.

In one embodiment, p is 1, 2, or 3. In one embodiment, p is 1 or 2.

Any of the groups described herein for any of $R_1$, $R_2$, $R_3$, $R_4$, $R_{S1}$, $R_{S2}$, $R_a$, $R_b$, $T_1$, $X_1$, L, m, n, and p can be combined with any of the groups described herein for one or more of the remainder of $R_1$, $R_2$, $R_3$, $R_a$, $R_{S1}$, $R_{S2}$, $R_a$, $R_b$, $T_1$, $X_1$, L, m, n, and p.

(1a) In one embodiment, $R_1$ is phenyl substituted with one or more $R_{S1}$; and each $R_{S1}$ independently is $C_1$-$C_6$ alkyl, $C_1$-$C_6$ haloalkyl, halogen, cyano, $OR_a$, $NR_aR_b$, $C(O)NR_aR_b$, $S(O)_2NR_aR_b$, or L-$T_1$, wherein at least one $R_{S1}$ is L-$T_1$.

(1b) In one embodiment, $R_1$ is phenyl substituted with one $R_{S1}$; and $R_{S1}$ is L-$T_1$.

(1c) In one embodiment, $R_1$ is phenyl substituted with two $R_{S1}$, and each $R_{S1}$ is L-$T_1$.

(1d) In one embodiment, $R_1$ is phenyl substituted with two $R_{S1}$; one $R_{S1}$ is L-$T_1$, and the other $R_{S1}$ is $C_1$-$C_6$ alkyl, $C_1$-$C_6$ haloalkyl, halogen, cyano, or $OR_a$.

(1e) In one embodiment, $R_1$ is phenyl substituted with one $R_{S1}$; and $R_{S1}$ is $S(O)_2NR_aR_b$.

(2a) In one embodiment, $R_1$ is heteroaryl as described herein substituted with one or more $R_{S1}$; and each $R_{S1}$ independently is $C_1$-$C_6$ alkyl, $C_1$-$C_6$ haloalkyl, halogen, cyano, $OR_a$, $NR_aR_b$, $C(O)NR_aR_b$, $S(O)_2NR_aR_b$, or L-$T_1$, wherein at least one $R_{S1}$ is L-$T_1$. In one embodiment, $R_1$ is pyridinyl or pyrazolyl.

(2b) In one embodiment, $R_1$ is heteroaryl as described herein substituted with one $R_{S1}$; and $R_{S1}$ is L-$T_1$. In one embodiment, $R_1$ is pyridinyl or pyrazolyl.

(2c) In one embodiment, $R_1$ is heteroaryl as described herein substituted with two $R_{S1}$; one $R_{S1}$ is L-$T_1$, and the other $R_{S1}$ is $C_1$-$C_6$ alkyl, $C_1$-$C_6$ haloalkyl, cyano, or $OR_a$. In one embodiment, $R_1$ is pyridinyl.

(2d) In one embodiment, $R_1$ is heteroaryl as described herein substituted with one $R_{S1}$; and $R_{S1}$ is $C_1$-$C_6$ haloalkyl. In one embodiment, $R_1$ is pyrazolyl.

(3a) In one embodiment, L is a bond, —C(O)—, —C(O)NH—, or —(CH$_2$)$_p$—.

(3b) In one embodiment, L is a bond, —C(O)—, or —(CH$_2$)$_p$—.

(3c) In one embodiment, L is a bond, —S(O)$_n$—, or —S(O)$_n$NH—.

(4a) In one embodiment, $R_1$ and $R_{S1}$ are as described and/or combined in any of (1a)-(2d); and L is a bond, —C(O)—, —C(O)NH—, or —(CH$_2$)$_p$—.

(4b) In one embodiment, $R_1$ and $R_{S1}$ are as described and/or combined in any of (1a)-(2d); L is a bond, —C(O)—, or —(CH$_2$)$_p$—.

(4c) In one embodiment, $R_1$ and $R_{S1}$ are as described and/or combined in any of (1a)-(2d); L is a bond, —S(O)$_n$—, or —S(O)$_n$NH—.

(5a) In one embodiment, $R_1$, $R_{S1}$, and L are as described and/or combined, where applicable, in any of (1a)-(4c), $T_1$ is $C_3$-$C_8$ cycloalkyl selected from cyclopropyl, cyclobutyl, cyclopentyl, cyclohexyl, cycloheptyl, and cyclooctyl, each optionally substituted with one or more $X_1$.

(5b) In one embodiment, $R_1$, $R_{S1}$, and L are as described and/or combined, where applicable, in any of (1a)-(4c), $T_1$ is heterocyclyl comprising one 5- or 6-membered ring and 1-4 heteroatoms selected from N, O, and S (e.g., pyrrolidinyl, pyrazolinyl, pyrazolidinyl, imidazolinyl, imidazolidinyl, piperidinyl, piperazinyl, or morpholinyl), optionally substituted with one or more $X_1$.

(5c) In one embodiment, $R_1$, $R_{S1}$, and L are as described and/or combined, where applicable, in any of (1a)-(4c), $T_1$ is heterocyclyl comprising one 6-membered ring and 1-4 heteroatoms selected from N, O, and S (e.g., piperidinyl, piperazinyl, or morpholinyl), optionally substituted with one or more $X_1$.

(6a) In one embodiment, $R_1$, $R_{S1}$, L, and $T_1$ are as described and/or combined, where applicable, in any of (1a)-(5c); and each $X_1$ independently is $C_1$-$C_6$ alkyl, $C_1$-$C_6$ haloalkyl, halogen, cyano, $OR_a$, $NR_aR_b$, $C(O)OR_a$, $C(O)NR_aR_b$, $S(O)_nOR_a$, or $S(O)_nNR_aR_b$.

(6b) In one embodiment, $R_1$, $R_{S1}$, L, and $T_1$ are as described and/or combined, where applicable, in any of (1a)-(5c); and each $X_1$ independently is $C_3$-$C_8$ cycloalkyl, $C_6$-$C_{10}$ aryl, heterocyclyl comprising one or two 5- or 6-membered rings and 1-4 heteroatoms selected from N, O, and S, or heteroaryl comprising one or two 5- or 6-membered rings and 1-4 heteroatoms selected from N, O, and S, wherein the cycloalkyl, aryl, heterocyclyl, or heteroaryl is optionally substituted with one or more $R_{S2}$.

(6c) In one embodiment, $R_1$, $R_{S1}$, L, and $T_1$ are as described and/or combined, where applicable, in any of (1a)-(5c); and each $X_1$ independently is $C_1$-$C_6$ alkyl, $C_1$-$C_6$ haloalkyl, halogen, cyano, $OR_a$, $C_3$-$C_8$ cycloalkyl, $C_6$-$C_{10}$ aryl, heterocyclyl comprising one or two 5- or 6-membered rings and 1-4 heteroatoms selected from N, O, and S, or heteroaryl comprising one or two 5- or 6-membered rings and 1-4 heteroatoms selected from N, O, and S, wherein the cycloalkyl, aryl, heterocyclyl, or heteroaryl is optionally substituted with one or more $R_{S2}$.

(6d) In one embodiment, $R_1$, $R_{S1}$, L, and $T_1$ are as described and/or combined, where applicable, in any of (1a)-(5c); and each $X_1$ independently is $C_1$-$C_6$ alkyl, $C_1$-$C_6$ haloalkyl, halogen, cyano, $OR_a$, $C_3$-$C_8$ cycloalkyl, or heterocyclyl comprising one or two 5- or 6-membered rings and 1-4 heteroatoms selected from N, O, and S, wherein the cycloalkyl or heterocyclyl is optionally substituted with one or more $R_{S2}$.

(7a) In one embodiment, $R_1$, $R_{S1}$, L, $T_1$, and $X_1$ are as described and/or combined, where applicable, in any of (1a)-(6d); and $R_2$ is H.

(7b) In one embodiment, $R_1$, $R_{S1}$, L, $T_1$, and $X_1$ are as described and/or combined, where applicable, in any of (1a)-(6d); and $R_2$ is $C_1$-$C_6$ alkyl.

(8) In one embodiment, $R_1$, $R_{S1}$, L, $T_1$, and $X_1$ are as described and/or combined, where applicable, in any of (1a)-(6d); and $R_3$ is $C_1$-$C_6$ alkyl.

(9a) In one embodiment, $R_1$, $R_{S1}$, L, $T_1$, and $X_1$ are as described and/or combined, where applicable, in any of (1a)-(6d); and $R_3$ is $C_1$-$C_6$ alkyl; and $R_2$ is H.

(9b) In one embodiment, $R_1$, $R_{S1}$, L, $T_1$, and $X_1$ are as described and/or combined, where applicable, in any of (1a)-(6d); and $R_2$ and $R_3$ are each independently $C_1$-$C_6$ alkyl.

(10a) In one embodiment, $R_1$, $R_2$, $R_3$, $R_{S1}$, L, $T_1$, and $X_1$ are as described and/or combined, where applicable, in any of (1a)-(9b); and m is 1, 2, 3, or 4.

(10b) In one embodiment, $R_1$, $R_2$, $R_3$, $R_{S1}$, L, $T_1$, and $X_1$ are as described and/or combined, where applicable, in any of (1a)-(9b); and m is 0, 1, or 2.

(10c) In one embodiment, $R_1$, $R_2$, $R_3$, $R_{S1}$, L, $T_1$, and $X_1$ are as described and/or combined, where applicable, in any of (1a)-(9b); and m is 0.

In one embodiment, a compound of Formula I is of Formula Ib or Ib1:

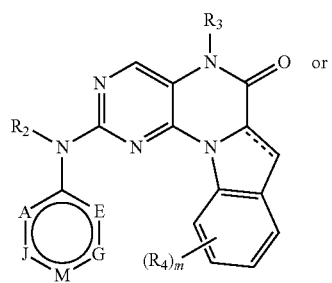

(Ib)

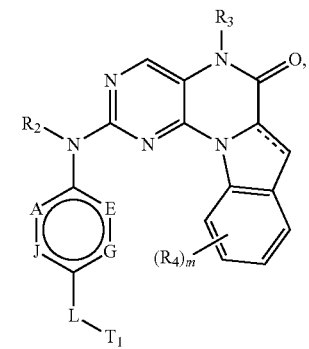

(Ib1)

or a pharmaceutically acceptable salt thereof, wherein A, E, G, J, and M are each independently CH, $CR_{S1}$, or N; and $R_2$, $R_3$, $R_4$, $R_{S1}$, $R_{S2}$, $R_a$, $R_b$, $T_1$, $X_1$, L, m, n, and p are each as defined in Formula I.

For a compound of Formula Ib or 1b, where applicable:

In one embodiment, one of A, E, G, J, and M is $CR_{S1}$, and the remaining of A, E, G, J, and M are each CH. In one embodiment, M is $CR_{S1}$, and A, E, G, and J are each CH.

In one embodiment, two of A, E, G, J, and M are independently $CR_{S1}$, and the remaining of A, E, G, J, and M are each CH. In one embodiment, J and G are independently $CR_{S1}$, and A, E, and M are each CH.

In one embodiment, one of A, E, G, J, and M is N, one of A, E, G, J, and M is $CR_{S1}$, and the remaining of A, E, G, J, and M are each CH. In one embodiment, M is $CR_{S1}$, one of A, E, G, and J is N, and the remaining of A, E, G, and J are each CH.

$R_2$, $R_3$, $R_4$, $R_{S1}$, $R_{S2}$, $R_a$, $R_b$, $T_1$, $X_1$, L, m, n, and p can be any of the groups described herein, such as in Formula I.

Any of the groups described herein for any of A, E, G, J, and M can be combined with any of the groups described herein for one or more of the remainder of A, E, G, J, and M, and can further be combined with any of the groups described herein for one or more of $R_2$, $R_3$, $R_4$, $R_{S1}$, $R_{S2}$, $R_a$, $R_b$, $T_1$, $X_1$, L, m, n, and p.

In one embodiment, a compound of Formula I is of Formula Ic or Ic1:

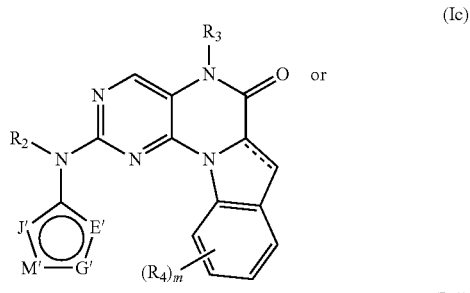

(Ic)

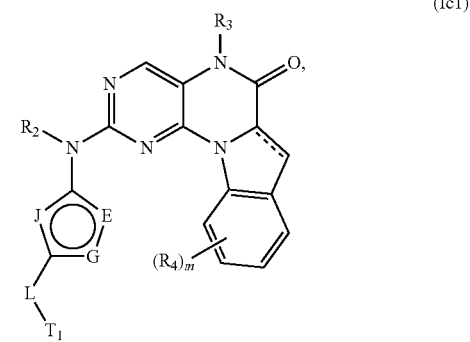

(Ic1)

or a pharmaceutically acceptable salt thereof, wherein E', G', J', and M' are each independently CH, $CR_{S1}$, $NR_{S1}$, or N; and $R_2$, $R_3$, $R_4$, $R_{S1}$, $R_{S2}$, $R_a$, $R_b$, $T_1$, $X_1$, L, m, n, and p are each as defined in Formula I.

For a compound of Formula Ic or Ic1, where applicable:

In one embodiment, one of E', G', J', and M' is $CR_{S1}$, one of E', G', J', and M' is N, and the remaining of E', G', J', and M' are each CH. In one embodiment, M' is $CR_{S1}$, one of E', G', and J' is N, and the remaining of E', G', and J' are each CH.

In one embodiment, one of E', G', J', and M' is $NR_{S1}$, one of E', G', J', and M' is N, and the remaining of E', G', J', and M' are each CH. In one embodiment, M' is $NR_{S1}$, one of E', G', and J' is N, and the remaining of E', G', and J' are each CH.

$R_2$, $R_3$, $R_4$, $R_{S1}$, $R_{S2}$, $R_a$, $R_b$, $T_1$, $X_1$, L, m, n, and p can be any of the groups described herein, such as in Formula I.

Any of the groups described herein for any of E', G', J', and M' can be combined with any of the groups described herein for one or more of the remainder of E', G', J', and M', and can further be combined with any of the groups described herein for one or more of $R_2$, $R_3$, $R_4$, $R_{S1}$, $R_{S2}$, $R_a$, $R_b$, $T_1$, $X_1$, L, m, n, and p.

In one embodiment, a compound of Formula I is of any of Formula Id1-Id8:

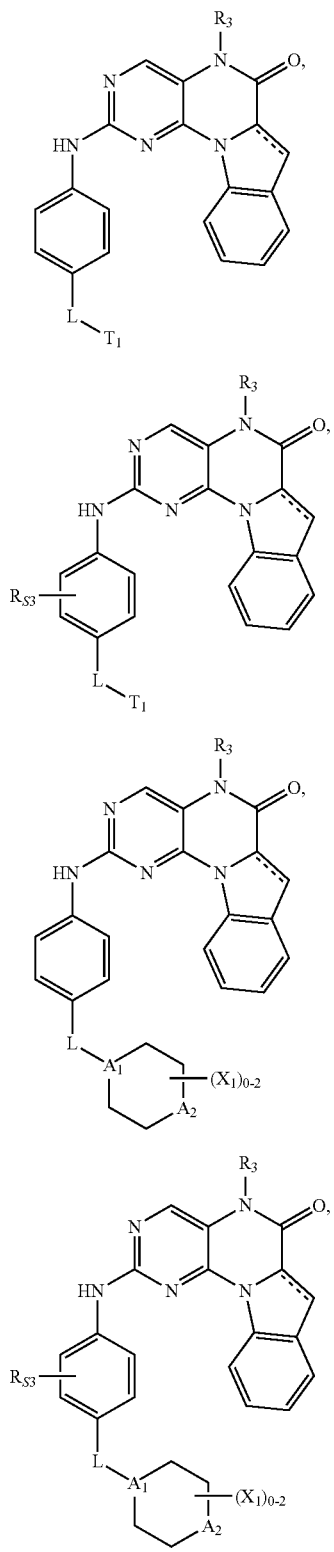

(Id1)

(Id2)

(Id3)

(Id4)

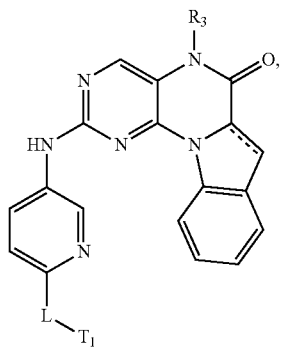

(Id5)

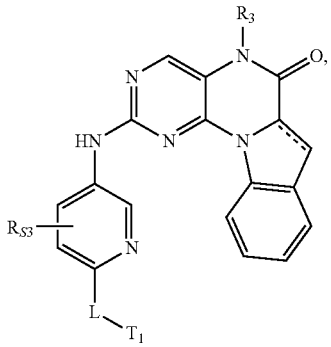

(Id6)

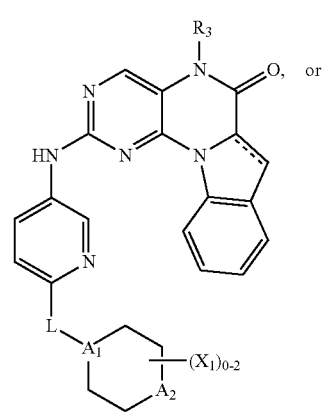

(Id7)

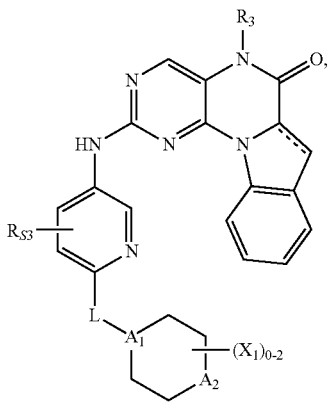

(Id8)

or pharmaceutically acceptable salt thereof, wherein
$A_1$ is CH or N;
$A_2$ is $CH_2$, $CHX_1$, NH, $NX_1$, or O;
$R_{S3}$ is $C_1$-$C_6$ alkyl, $C_1$-$C_6$ haloalkyl, halogen, cyano, $OR_a$, $NR_aR_b$, $C(O)NR_aR_b$, or $S(O)_2NR_aR_b$; and $R_3$, $R_{S2}$, $R_a$, $R_b$, $T_1$, $X_1$, L, n, and p are each as defined in Formula I.

For a compound of any of Formula Id1-Id8, where applicable:

In one embodiment, $R_{S3}$ is $C_1$-$C_6$ alkyl (e.g., methyl, ethyl, n-propyl, i-propyl, n-butyl, i-butyl, s-butyl, t-butyl, pentyl, or hexyl) or $C_1$-$C_6$ haloalkyl (e.g., methyl, ethyl, n-propyl, i-propyl, n-butyl, i-butyl, s-butyl, t-butyl, pentyl, or hexyl, each substituted with one or more halogen (e.g., F, Cl, Br, or I)), halogen (e.g., F, Cl, Br, or I), cyano, or $OR_a$.

In one embodiment, $A_1$ is CH.

In one embodiment, $A_1$ is N.

In one embodiment, $A_2$ is $CH_2$ or $CHX_1$. In one embodiment, $A_2$ is $CH_2$. In one embodiment, $A_2$ is $CHX_1$.

In one embodiment, $A_2$ is NH or $NX_1$. In one embodiment, $A_2$ is NH. In one embodiment, $A_2$ is $NX_1$.

In one embodiment, $A_2$ is O.

In one embodiment, $A_1$ is CH; and $A_2$ is $CH_2$ or $CHX_1$. In a further embodiment, $A_2$ is $CH_2$. In another further embodiment, $A_2$ is $CHX_1$.

In one embodiment, $A_1$ is N; and $A_2$ is $CH_2$ or $CHX_1$. In a further embodiment, $A_2$ is $CH_2$. In another further embodiment, $A_2$ is $CHX_1$.

In one embodiment, $A_1$ is N; and $A_2$ is O.

In one embodiment, $R_{S3}$ is methyl, $CF_3$, F, Cl, or $OR_a$.

In one embodiment, $R_{S3}$ is halogen (e.g., F, Cl, Br, or I), cyano, $OR_a$, $NR_AR_b$, $C(O)NR_AR_b$, or $S(O)_2NR_AR_b$.

$R_3$, $R_{S2}$, $R_a$, $R_b$, $T_1$, $X_1$, L, n, and p can be any of the groups described herein, such as in Formula I.

Any of the groups described herein for any of $A_1$, $A_2$, and $R_{S3}$ can be combined with any of the groups described herein for one or more of the remainder of $A_1$, $A_2$, and $R_{S3}$, and can further be combined with any of the groups described herein for one or more of $R_3$, $R_{S2}$, $R_a$, $R_b$, $T_1$, $X_1$, L, n, and p.

Non-limiting illustrative compounds of the application are listed in Table 1.

TABLE 1

| Cmpd ID | Structure |
|---------|-----------|
| I-1 | |
| I-2 | 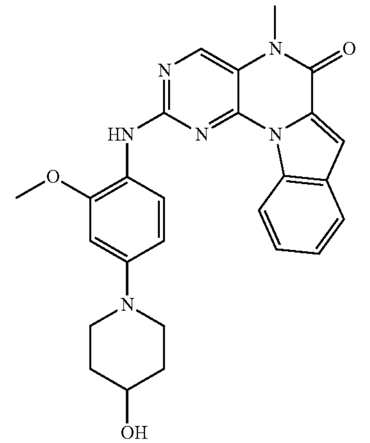 |
| I-3 | 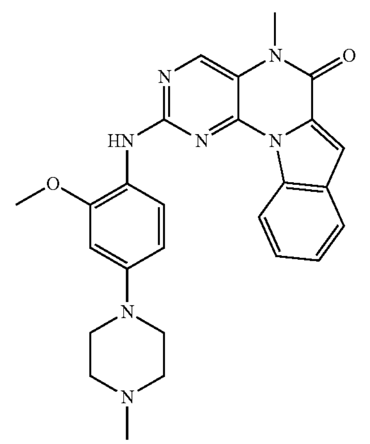 |
| I-4 | 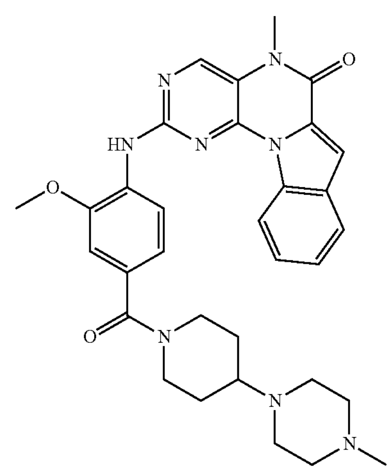 |

TABLE 1-continued

| Cmpd ID | Structure |
|---|---|
| I-5 | (structure) |
| I-6 | (structure) |
| I-7 | (structure) |
| I-8 | (structure) |
| I-9 | (structure) |
| I-10 | (structure) |

TABLE 1-continued

| Cmpd ID | Structure |
|---|---|
| I-11 | 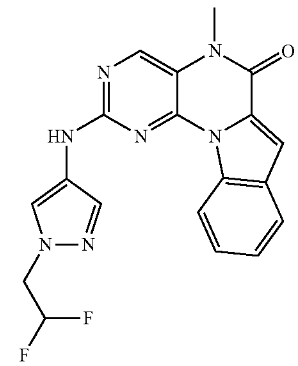 |
| I-12 | 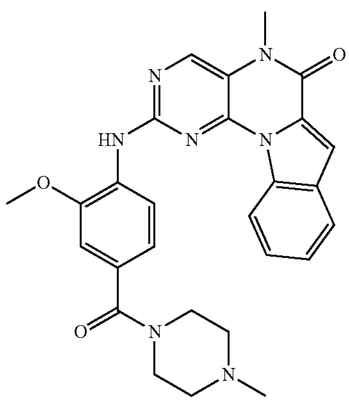 |
| I-13 | 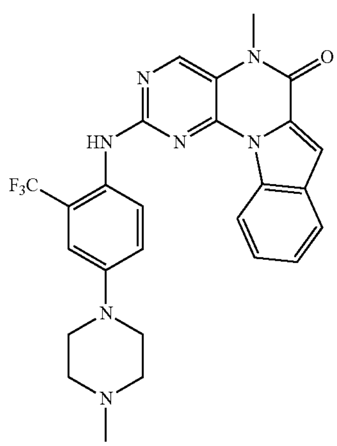 |
| I-14 | 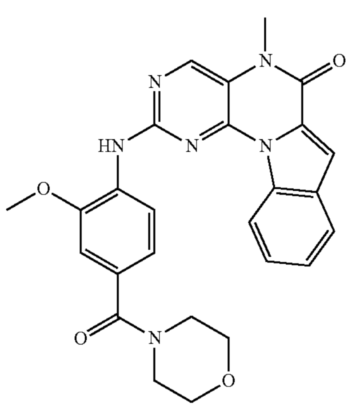 |
| I-15 | |
| I-16 | |
| I-17 | |

TABLE 1-continued

| Cmpd ID | Structure |
|---|---|
| I-18 | 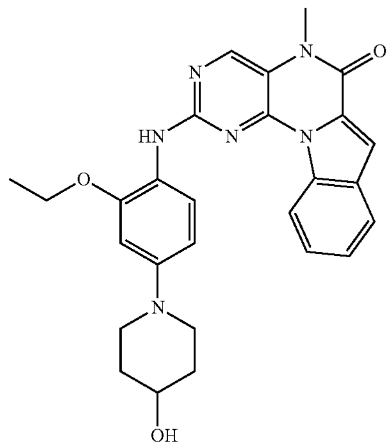 |
| I-19 | 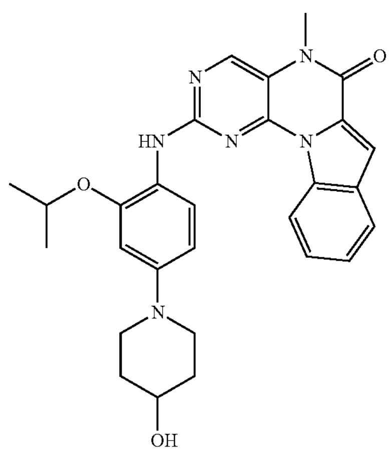 |
| I-20 | 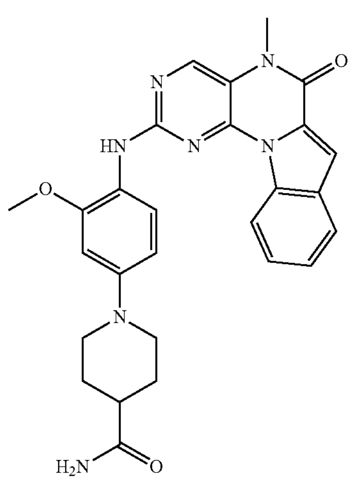 |
| I-21 | |
| I-22 | |
| I-23 | |

TABLE 1-continued

| Cmpd ID | Structure |
|---|---|
| I-24 | 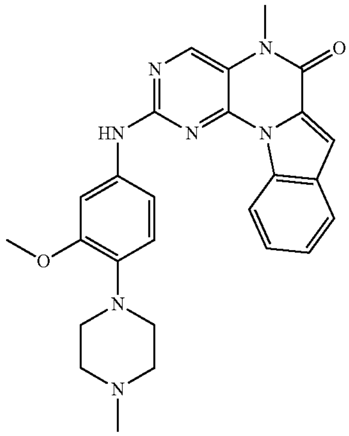 |
| I-25 | 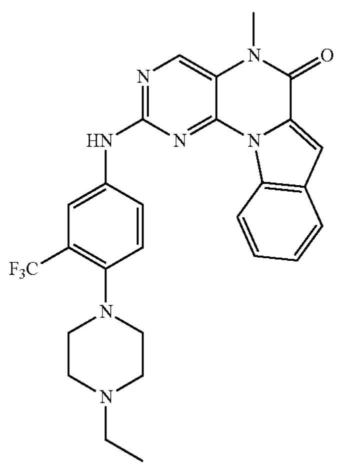 |
| I-26 | 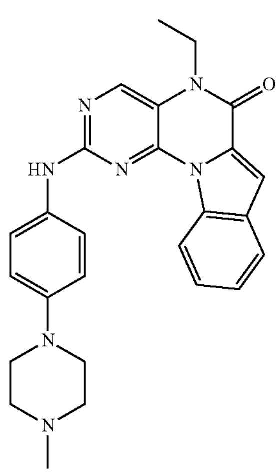 |
| I-27 | |
| I-28 | |
| I-29 | |

TABLE 1-continued

| Cmpd ID | Structure |
|---|---|
| I-30 | 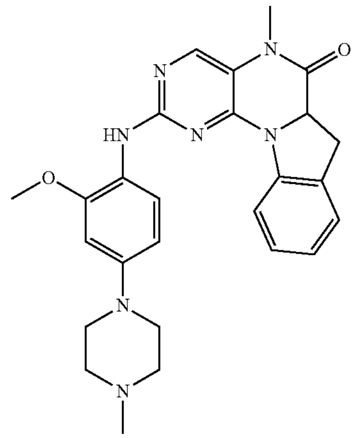 |
| I-31 | 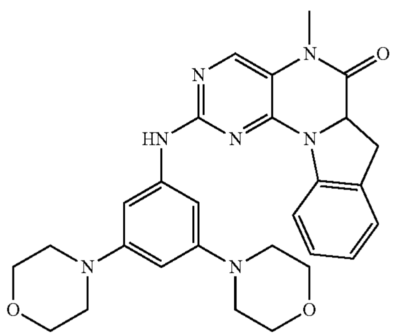 |
| I-32 | 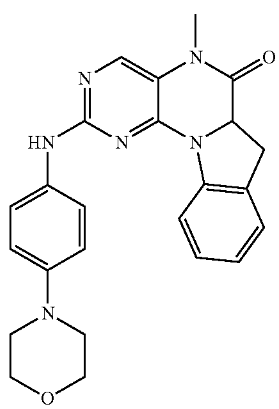 |
| I-33 | 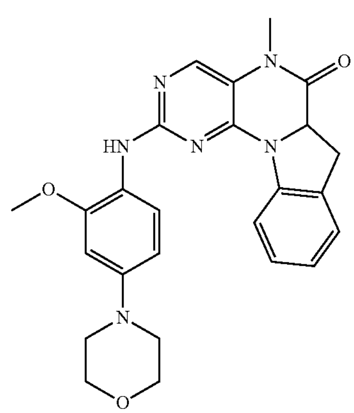 |

Some of the foregoing compounds can comprise one or more asymmetric centers, and thus can exist in various isomeric forms, e.g., stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{18}F$, $^3S$, $^{32}P$, $^{125}I$, and $^{131}I$) introduced into the compound. Such compounds are useful for drug metabolism studies and diagnostics, as well as therapeutic applications.

A compound of the application may be prepared as a pharmaceutically acceptable salt (e.g., protonated) by reacting the free base form of the compound with a pharmaceutically acceptable inorganic or organic acid. Alternatively, a pharmaceutically acceptable salt (e.g., deprotonated) of a compound of the application can be prepared by reacting the free acid form of the compound with a pharmaceutically acceptable inorganic or organic base. The pharmaceutically acceptable salt may include various counterions, e.g., counterions of the inorganic or organic acid, counterions of the inorganic or organic base, or counterions afforded by counterion exchange.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In one embodiment, the substantially similar conditions comprise determining a NEK-dependent phosphorylation level, in vitro or in vivo (e.g., in cells expressing a wild-type NEK, a mutant NEK, or a fragment of any thereof).

In one embodiment, the compounds of the present application are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer (e.g., non-small cell lung cancer), melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, and T-cell lymphoma.

A "selective NEK inhibitor" can be identified, for example, by comparing the ability of a compound to inhibit NEK kinase activity to its ability to inhibit the other kinases. In one embodiment, the selectivity can be identified by measuring the $EC_{50}$ or $IC_{50}$ of the compounds.

In one embodiment, the compounds of the application are NEK inhibitors that exhibit at least 2-fold, 3-fold, 5-fold, 10-fold, 25-fold, 50-fold, or 100-fold selectivity over other kinases. In one embodiment, the compounds of the application exhibit 1000-fold selectivity over other kinases.

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application may be synthesized according to the following general scheme, using various starting materials and intermediates available in the art under appropriate reaction conditions. Representative reaction conditions include the following: (I) DIPEA, DMF, 60° C.; (II) Fe/HOAc, 50° C.; (III) MeI/C$_{S2}$CO$_3$, DMA, 0° C.; (IV) DDQ, benzene, 100° C.; and (V) X-Phos (9 mol %), Pd2(dba)3 (6 mol %), Cs2CO3, 1,4-dioxane, 100° C.

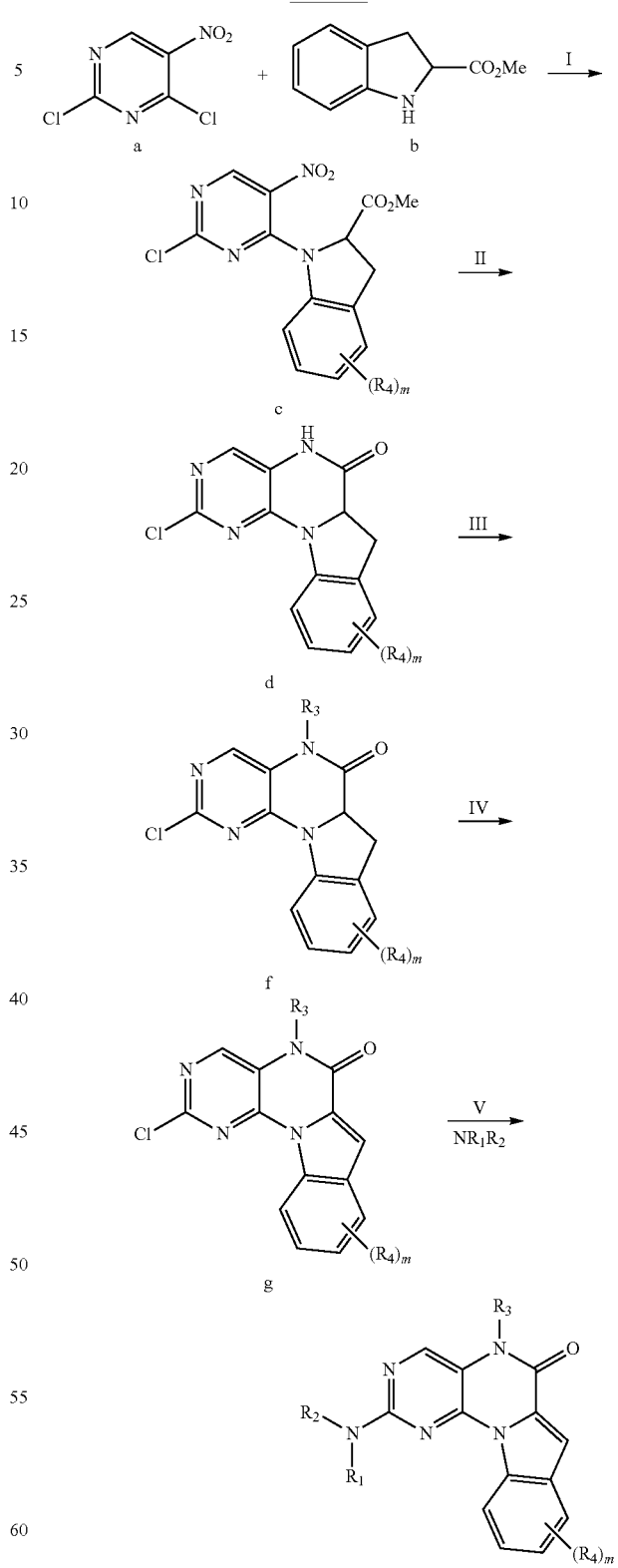

Pharmaceutical Compositions

In another aspect, a pharmaceutical composition is provided. The pharmaceutical composition comprises a therapeutically effective amount of a compound of the application, or a pharmaceutically acceptable salt thereof, and a pharmaceutically acceptable carrier.

Compounds of the application may be administered as pharmaceutical compositions by any conventional route, in particular enterally, e.g., orally, e.g., in the form of tablets or capsules, or parenterally, e.g., in the form of injectable solutions or suspensions, or topically, e.g., in the form of lotions, gels, ointments or creams, or in a nasal or suppository form.

Pharmaceutical compositions including a compound of the present application in free form or in a pharmaceutically acceptable salt form in association with at least one pharmaceutically acceptable carrier or diluent may be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier may include absorbable pharmacologically acceptable solvents to assist passage through the skin of the host. For example, transdermal devices may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which may serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application may be administered to humans and other animals orally, rectally, parenterally, intracisternally, intravaginally, intraperitoneally, topically (as by powders, ointments, or drops), buccally, or as an oral or nasal spray.

Liquid dosage forms for oral administration may include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds may also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Methods of Use

In one aspect, the present application provides a method of modulating (e.g., inhibiting) NEK. The method comprises administering to a subject in need thereof a therapeutically effective amount of a compound of the application or an enantiomer, diastereomer, stereoisomer, or pharmaceutically acceptable salt thereof, or a pharmaceutical composition of the application.

In one embodiment, the inhibition of NEK activity is measured by $IC_{50}$. In one embodiment, the inhibition of NEK activity is measured by $EC_{50}$.

A compound of the present application (e.g., a compound of any of the formulae described herein, or selected from any compounds described herein) is capable of treating or preventing a disease or disorder in which NEK plays a role or in which NEK is deregulated (e.g., overexpressed).

In one aspect, the present application provides a method of treating or preventing a disease responsive to modulation of NEK. The method comprises administering to a subject in need thereof a therapeutically effective amount of a compound of the application or an enantiomer, diastereomer, stereoisomer, or pharmaceutically acceptable salt thereof, or a pharmaceutical composition of the application.

In one aspect, the present application provides a method of treating or preventing a disease. The method comprises administering to a subject in need thereof a therapeutically effective amount of a compound of the application or an enantiomer, diastereomer, stereoisomer, or pharmaceutically acceptable salt thereof, or a pharmaceutical composition of the application. In one aspect, the disease is a NEK mediated disorder. In one aspect, the disease is a proliferative disease (e.g., a proliferative disease in which NEK plays a role).

In one aspect, the present application provides a method of treating or preventing cancer in a subject, wherein the cell of the cancer comprises an activated NEK or wherein the subject is identified as being in need of inhibition of NEK for the treatment or prevention of cancer. The method comprises administering to the subject a therapeutically effective amount of a compound of the application or an enantiomer, diastereomer, stereoisomer, or pharmaceutically acceptable salt thereof, or a pharmaceutical composition of the application.

In one embodiment, the disease (e.g., cancer) is mediated by NEK (e.g., NEK plays a role in the initiation or development of the disease).

In one embodiment, the NEK activation is selected from mutation of NEK, amplification of NEK, overexpression of NEK, and ligand mediated activation of NEK.

In one embodiment, the present application provides a method of treating or preventing any of the diseases, disorders, and conditions described herein, wherein the subject is a human. In one embodiment, the application provides a method of treating. In one embodiment, the application provides a method of preventing.

As inhibitors of NEK, the compounds and compositions of this application are particularly useful for treating or lessening the severity of a disease, condition, or disorder where a protein kinase is implicated in the disease, condition, or disorder. In one embodiment, the present application provides a method for treating or lessening the severity of a disease, condition, or disorder where a protein kinase is implicated in the disease state. In one embodiment, the present application provides a method for treating or lessening the severity of a kinase disease, condition, or disorder where inhibition of enzymatic activity is implicated in the treatment of the disease. In one embodiment, the present application provides a method for treating or lessening the severity of a disease, condition, or disorder with compounds that inhibit enzymatic activity by binding to the protein kinase. In one embodiment, the present application provides a method for treating or lessening the severity of a kinase disease, condition, or disorder by inhibiting enzymatic activity of the kinase with a protein kinase inhibitor.

In one embodiment, the disease or disorder is cancer or a proliferation disease.

In one embodiment, the disease or disorder is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In one embodiment, the disease or disorder is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, peripheral neuropathy, or B-Cell Lymphoma.

In one embodiment, the disease or disorder is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, or lymphoma.

In one embodiment, the disease or disorder is selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In one embodiment, the disease or disorder is selected from a proliferative disorder and a neurodegenerative disorder.

In one embodiment, the disease or disorder is characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer.

The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" also refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Cancer may also include colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

Cancer may also include colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In one embodiment, the compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes *dorsalis*, and Toxic encephalopathy.

In one aspect, the present application also provides a method of treating or preventing cell proliferative disorders such as hyperplasias, dysplasias, or pre-cancerous lesions. Dysplasia is the earliest form of pre-cancerous lesion recognizable in a biopsy by a pathologist. The compounds of the present application may be administered for the purpose of preventing hyperplasias, dysplasias, or pre-cancerous lesions from continuing to expand or from becoming cancerous. Examples of pre-cancerous lesions may occur in skin, esophageal tissue, breast, and cervical intra-epithelial tissue.

As inhibitors of NEK, the compounds and compositions of this application are also useful in assessing, studying, or testing biological samples. One aspect of the application relates to inhibiting protein kinase activity in a biological sample, comprising contacting the biological sample with a compound or a composition of the application.

The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ transplantation, and biological specimen storage.

Another aspect of this application relates to the study of NEK in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds and compositions of the present application as NEK inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this application as an inhibitor of various kinases are set forth in the Examples below.

In accordance with the foregoing, the present application provides a method for preventing or treating any of the diseases or disorders described above in a subject in need of such treatment, comprising administering to the subject a therapeutically effective amount of a compound of the application or an enantiomer, diastereomer, stereoisomer, or pharmaceutically acceptable salt thereof, or a pharmaceutical composition of the application. For any of the above uses, the required dosage will vary depending on the mode of administration, the particular condition to be treated and the effect desired.

Compounds and compositions of the application can be administered in therapeutically effective amounts in a combinational therapy with one or more therapeutic agents (pharmaceutical combinations) or modalities, e.g., anti-proliferative, anti-cancer, immunomodulatory or anti-inflammatory agent, and/or non-drug therapies, etc. For example, synergistic effects can occur with anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy may include the administration of the subject compounds in further combination with one or more other biologically active ingredients (such as, but not limited to, a second NEK inhibitor, a second and different antineoplastic agent, etc.) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one embodiment, the compounds may be administered in combination with one or more separate pharmaceutical agents, e.g., a chemotherapeutic agent, an immunotherapeutic agent, or an adjunctive therapeutic agent.

Another aspect of the present application relates to a kit comprising a compound of the application or a pharmaceutically acceptable salt thereof, or a pharmaceutical composition of the application.

Another aspect of the present application relates to a compound of the application or a pharmaceutically acceptable salt thereof, or a pharmaceutical composition of the application, for use in the manufacture of a medicament for modulating (e.g., inhibiting) NEK, for treating or preventing a disease (e.g., a disease in which NEK plays a role), or for treating or preventing cancer in a subject, wherein the cell of the cancer comprises an activated NEK or wherein the subject is identified as being in need of inhibition of NEK for the treatment or prevention of cancer.

Another aspect of the present application relates to use of a compound of the application or a pharmaceutically acceptable salt thereof, or a pharmaceutical composition of the application, in the manufacture of a medicament for modulating (e.g., inhibiting) NEK, for treating or preventing a disease (e.g., a disease in which NEK plays a role), or for treating or preventing cancer in a subject, wherein the cell of the cancer comprises an activated NEK or wherein the subject is identified as being in need of inhibition of NEK for the treatment or prevention of cancer.

Another aspect of the present application relates to a compound of the application or a pharmaceutically acceptable salt thereof, or a pharmaceutical composition of the application, for use in modulating (e.g., inhibiting) NEK, in treating or preventing a disease (e.g., a disease in which NEK plays a role), or in treating or preventing cancer in a subject, wherein the cell of the cancer comprises an activated NEK or wherein the subject is identified as being in need of inhibition of NEK for the treatment or prevention of cancer.

Another aspect of the present application relates to use of a compound of the application or a pharmaceutically acceptable salt thereof, or a pharmaceutical composition of the application, in modulating (e.g., inhibiting) NEK, in treating or preventing a disease (e.g., a disease in which NEK plays a role), or in treating or preventing cancer in a subject, wherein the cell of the cancer comprises an activated NEK or wherein the subject is identified as being in need of inhibition of NEK for the treatment or prevention of cancer.

Definitions

Listed below are definitions of various terms used in this application. These definitions apply to the terms as they are used throughout this specification and claims, unless otherwise limited in specific instances, either individually or as part of a larger group.

The term "alkyl," as used herein, refers to saturated, straight or branched-chain hydrocarbon radicals containing, in one embodiment, between one and six carbon atoms. Examples of C1-C6 alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in one embodiment, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphtyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N, zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, indazoyl, cinnolinyl, phthalazinyl, pyridazinyl, indolyl, acridinyl, benzoquinolinyl, pyrimidinyl, a purinyl, pyrrolopyrimidinyl, quinoxalinyl, quinazolinyl, indazolinyl, and phthalazinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_1$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_2$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_2$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{11}$-alkyl, —OCONH—$C_2$-$C_{12}$-alkenyl, —OCONH—$C_2$-$C_{12}$-alkenyl, —OCONH—$C_3$-$C_1$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_2$-alkyl, —$NHCO_2$—$C_2$-$C_{12}$-alkenyl, —$NHCO_2$—$C_2$-$C_2$-alkenyl, —$NHCO_2$—$C_3$-$C_{12}$-cycloalkyl, —$NHCO_2$-aryl, —$NHCO_2$-heteroaryl, —$NHCO_2$— heterocycloalkyl, NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH-heterocycloalkyl, —NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_2$-alkenyl, C(NH)NH—$C_3$-$C_2$-cycloalkyl, —C(NH)NH-aryl, —C(NH)NH-heteroaryl, —C(NH)NHheterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_2$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_1$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

It is understood that the aryls, heteroaryls, alkyls, and the like can be substituted.

The term "cancer" includes, but is not limited to, the following cancers: epidermoid Oral buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma, and Adrenal glands: neuroblastoma. Thus, the term "cancerous cell" as provided herein, includes a cell afflicted by any one of the above-identified conditions.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The terms "disease(s)", "disorder(s)", and "condition(s)" are used interchangeably, unless the context clearly dictates otherwise.

"NEK" refers to NIMA-related kinase. NEK1 to NEK11 are members of the NEK kinase family.

The term "therapeutically effective amount" of a compound or pharmaceutical composition of the application, as used herein, means a sufficient amount of the compound or pharmaceutical composition so as to decrease the symptoms of a disorder in a subject. As is well understood in the medical arts a therapeutically effective amount of a compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in. *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, 7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews,* 1996, 19, 1-15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center, e.g., carbon. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc. "Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

EXAMPLES

Analytical Methods, Materials, and Instrumentation

All reactions were monitored Waters Acquity UPLC/MS system (Waters PDA ex Detector, QDa Detector, Sample manager—FL, Binary Solvent Manager) using Acquity UPLC® BEH C18 column (2.1×50 mm, 1.7 μm particle size): solvent gradient=90% at 0 min, 1% A at 1.8 min; solvent A=0.1% formic acid in Water; solvent B=0.1% formic acid in Acetonitrile; flow rate: 0.6 mL/min. Reaction products were purified by flash column chromatography using CombiFlash®Rf with Teledyne Isco RediSep®Rf High Performance Gold or Silicycle SiliaSep™ High Performance columns (4 g, 12 g, 24 g, 40 g, or 80 g), Waters HPLC system using SunFire™ Prep C18 column (19×100 mm, 5 μm particle size): solvent gradient=80% A at 0 min, 5% A at 25 min; solvent A=0.035% TFA in Water; solvent B=0.035% TFA in MeOH; flow rate: 25 mL/min (Method A), and Waters Acquity UPLC/MS system (Waters PDA eλ Detector, QDa Detector, Sample manager—FL, Binary Solvent Manager) using Acquity UPLC® BEH C18 column (2.1×50 mm, 1.7 μm particle size): solvent gradient=80% A at 0 min, 5% A at 2 min; solvent A=0.1% formic acid in Water; solvent B=0.1% formic acid in Acetonitrile; flow rate: 0.6 m/min (method B). The purity of all compounds was over 95% and was analyzed with Waters LC/MS system. $^1$H NMR was obtained using a 500 MHz Bruker Avance III. Chemical shifts are reported relative to dimethyl sulfoxide (δ=2.50) for $^1$H NMR. Data are reported as (br=broad, s=singlet, d=doublet, t=triplet, q=quartet, m=multiplet).

Abbreviations used in the following examples and elsewhere herein are:
AcOH acetic acid
atm atmosphere
br broad
CuSO$_4$ copper sulfate
DCM dichloromethane
DIEA N,N-diisopropylethylamine
DMA N,N-dimethylacetamide
DMF N,N-dimethylformamide
DMSO dimethyl sulfoxide
EDCl 1-ethyl-3-(3-dimethylaminopropyl) carbodiimide
ESI electrospray ionization
EtOAc ethyl acetate
HCl hydrochloric acid
h hour(s)
HATU bis(dimethylamino)methylene]-1H-1,2,3-triazolo[4,5-b]pyridinium 3-oxide hexafluoro-phosphate
HPLC high-performance liquid chromatography
LCMS liquid chromatography-mass spectrometry
m multiplet
mL milliliter
MeCN acetonitrile
MeOH methanol
mg milligram
mmol millimole
MgSO4 magnesium sulfate
MHz megahertz
min minutes
MS mass spectrometry
Na2CO3 sodium carbonate
NMR nuclear magnetic resonance
Tf triflate
Pd2(dba)3 tris(dibenzylideneacetone)dipalladium(0)
Pd(PPh3)2Cl2 bis(triphenylphosphine)palladium(II) dichloride
PMe3 trimethylphosphine
ppm parts per million
rt room temperature
TBAF tetra-n-butylammonium fluoride
t-BuOH tert-butanol
TMS trimethylsilane
THF tetrahydrofuran
TLC thin layer chromatography
μL microliter
Xphos 2-dicyclohexylphosphino-2',4',6'-triisopropylbiphenyl Example 1: Synthesis of Compound I-1

Compound I-1 was prepared according to the following scheme.

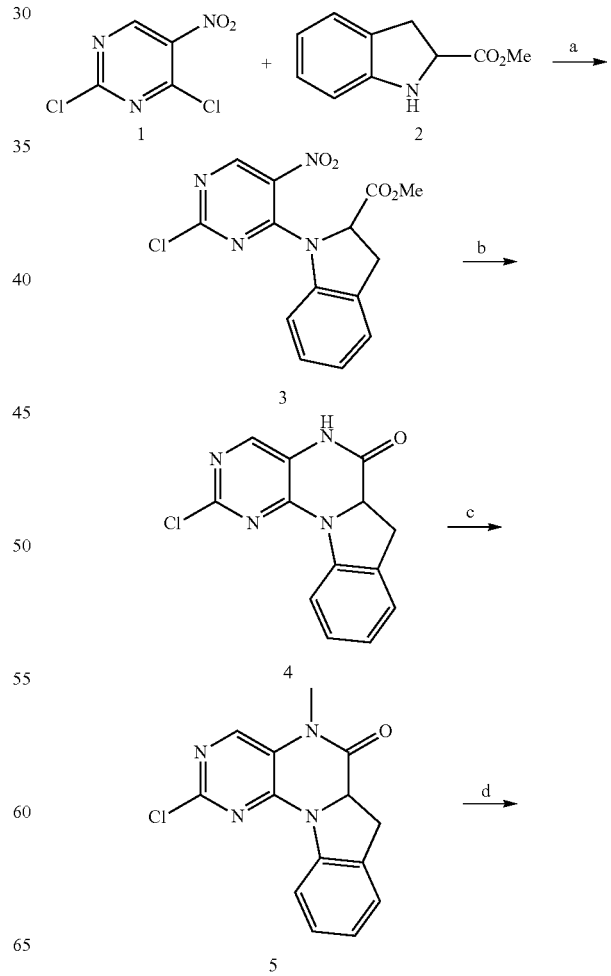

-continued

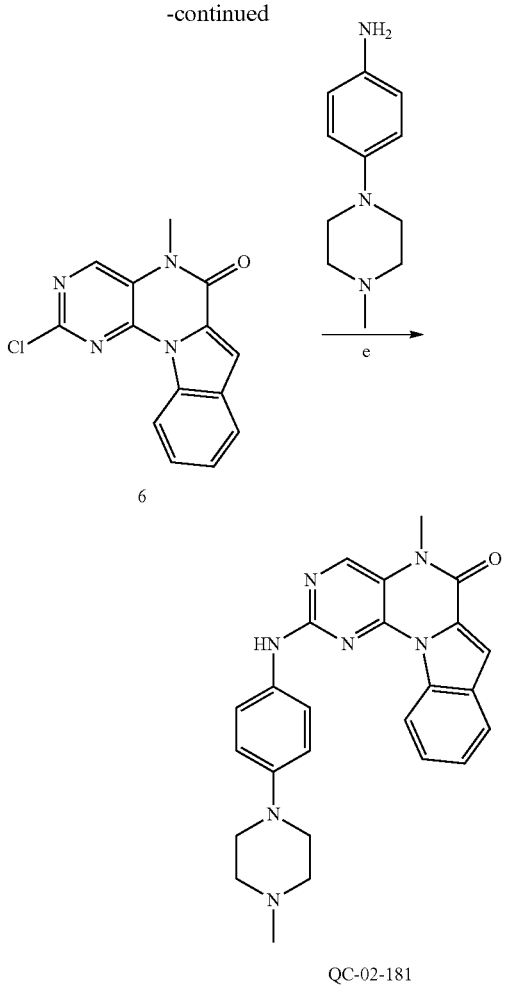

QC-02-181

Reagents and conditions:
(a) DIPEA, DMF, 60° C.; (b) Fe/HOAc, 50° C.; (c) MeI/Cs$_2$CO$_3$, DMA, 0° C.; (d) DDQ, benzene, 100° C.; (e) X-Phos (9 mol %), Pd$_2$(dba)$_3$ (6 mol %), Cs$_2$CO$_3$, 1,4-dioxane, 100° C.

Step 1: Synthesis of Compound 3

To a stirred solution of methyl indoline-2-carboxylate (828 mg, 4.70 mmol) and DIEA (1.36 mL, 7.80 mmol) in 12 mL of DMF was added 2,4-dichloro-5-nitropyrimidine (756.5 mg, 3.90 mmol) in one portion at room temperature. Then the reaction was stirred at 60° C. After the reaction was complete as monitored by LC-MS, the resulting mixture was diluted with ethyl acetate and washed with water and brine. The organic layer was dried over anhydrous sodium sulfate and concentrated. The residue was purified by silica-gel column chromatography to give the title Compound 3 (1.055 g, 81%).

Step 2: Synthesis of Compound 4

A mixture of Compound 3 (1.055 g, 3.07 mmol) and iron power (1.718 g, 30.7 mmol) in 18 mL of acetic acid was heated at 50° C. After the reaction was complete, the mixture was concentrated. Then the residue was purified by silica-gel column chromatography with methanol and dichloromethane (1/25, v/v) to give the title Compound 4 (734 mg, 2.70 mmol, 88%).

Step 3: Synthesis of Compound 5

To a stirred solution of Compound 4 (734 mg, 2.70 mmol) and MeI (422 mg, 2.97 mmol) in 13 mL of dimethyl acetamide (DMA) was added Cs$_2$CO$_3$ (1.320 g, 4.05 mmol) at 0° C. The reaction mixture was stirred at this temperature. After the reaction was complete as monitored by LC-MS, the resulting mixture was diluted with ethyl acetate and washed with water and brine. The organic layer was dried over anhydrous sodium sulfate and concentrated. The residue was purified by silica-gel column chromatography to give the title Compound 5 (710 mg, 2.48 mmol, 92%).

Step 4: Synthesis of Compound 6

To a stirred solution of Compound 5 (355 mg, 1.24 mmol) in 12 mL of benzene was added DDQ (563 mg, 2.48 mmol) in one portion at room temperature. Then the reaction was stirred at 100° C. After the reaction was complete as monitored by LC-MS, the resulting mixture was diluted with ethyl acetate and washed with water and brine. The organic layer was dried over anhydrous sodium sulfate and concentrated. The residue was purified by Reverse-Phase HPLC to give the title Compound 6 (299 mg, 1.05 mmol, 85% yield).

Step 5: Synthesis of Compound I-1

A mixture of 6 (34 mg, 0.12 mmol), 4-(4-methylpiperazin-1-yl)benzen-amine (23 mg, 0.12 mmol), X-Phos (5.1 mg), Pd$_2$(dba)$_3$ (6.6 mg) and Cs$_2$CO$_3$ (78 mg, 0.24 mmol) in 1.5 mL of 1,4-dioxane was heated at 110° C. in a seal tube for 3 h. Then the reaction was filtered through celite and eluted with dichloromethane. Concentrated and the residue was purified by reverse-phase prep-HPLC using a water (0.05% TFA)/acetonitrile (0.05% TFA) gradient to afford Compound I-1 as TFA salt (28 mg, 0.05 mmol, 42%). $^1$H NMR (500 MHz, DMSO-d6) δ 9.70 (s, 1H), 9.60 (s, 1H), 9.08 (d, J=8.2 Hz, 1H), 8.59 (s, 1H), 7.90 (d, J=7.9 Hz, 1H), 7.65 (d, J=8.9 Hz, 2H), 7.55-7.50 (m, 3H), 7.46-7.42 (m, 1H), 7.06 (d, J=9.0 Hz, 2H), 3.81 (d, J=13.0 Hz, 2H), 3.59 (s, 3H), 3.55 (d, J=11.9 Hz, 2H), 3.27-3.15 (m, 2H), 2.95 (t, J=12.1 Hz, 2H), 2.89 (s, 3H).

Example 2: Synthesis of Compounds of the Present Application

Using the appropriate starting materials and/or intermediates, compounds of the application can be prepared according to the synthetic schemes and examples described herein. Representative compounds are listed below.

Compound I-5: $^1$H NMR (500 MHz, DMSO-d$_6$) δ 10.07 (s, 1H), 9.82 (s, 1H), 9.08 (d, J=8.3 Hz, 1H), 8.64 (s, 1H), 8.27 (d, J=2.4 Hz, 1H), 7.99 (dd, J=8.7, 2.0 Hz, 1H), 7.91 (d, J=7.9 Hz, 1H), 7.60 (d, J=8.7 Hz, 1H), 7.56 (s, 1H), 7.53 (t, J=7.7 Hz, 1H), 7.46 (t, J=7.1 Hz, 1H), 3.60 (s, 3H), 3.53 (d, J=9.4 Hz, 3H), 3.19-3.09 (m, 6H), 2.91 (d, J=3.2 Hz, 3H).

Compound I-6: $^1$H NMR (500 MHz, DMSO-d$_6$) 9.52 (s, 1H), 8.78 (d, J=7.2 Hz, 1H), 8.75 (s, 1H), 8.54 (s, 1H), 7.88 (dd, J=6.3, 2.4 Hz, 1H), 7.74 (d, J=8.1 Hz, 1H), 7.52 (s, 1H), 7.46-7.33 (m, 2H), 6.99 (d, J=1.6 Hz, 1H), 6.90 (dd, J=8.1, 1.6 Hz, 1H), 3.82 (s, 3H), 3.61-3.48 (m, 5H), 3.16-3.05 (m, 2H), 2.93-2.81 (m, 4H), 2.12 (d, J=14.0 Hz, 2H), 1.93 (qd, J=14.0, 3.8 Hz, 2H).

Compound I-7: $^1$H NMR (500 MHz, DMSO-d$_6$) 9.70 (s, 1H), 9.60 (s, 1H), 9.08 (d, J=8.2 Hz, 1H), 8.57 (s, 1H), 7.90 (d, J=7.9 Hz, 1H), 7.65 (d, J=8.9 Hz, 2H), 7.55-7.49 (m, 2H), 7.47-7.39 (m, 1H), 7.06 (d, J=9.0 Hz, 2H), 3.81 (d, J=13.0

Hz, 2H), 3.59 (s, 5H), 3.21 (dd, J=9.9, 9.4 Hz, 2H), 2.95 (t, J=12.1 Hz, 2H), 2.89 (s, 3H).

Compound I-9: ¹H NMR (500 MHz, DMSO-d₆) δ 8.77 (s, 1H), 8.65 (s, 1H), 8.50 (s, 1H), 7.87 (dd, J=6.5, 2.2 Hz, 1H), 7.61-7.47 (m, 2H), 7.45-7.30 (m, 2H), 6.80 (s, 1H), 6.73-6.60 (m, 1H), 3.88 (d, J=11.8 Hz, 2H), 3.79 (s, 3H), 3.57 (s, 3H), 2.81 (br, 6H), 2.07 (d, J=8.0 Hz, 2H), 1.79-1.65 (m, 2H).

Compound I-10: ¹H NMR (500 MHz, DMSO-d₆) δ 10.02 (s, 1H), 9.73 (s, 1H), 9.12 (s, 1H), 8.54 (s, 1H), 8.11 (s, 1H), 7.91 (dd, J=8.0, 1.1 Hz, 1H), 7.72 (s, 1H), 7.61-7.52 (m, 2H), 7.46 (ddd, J=8.0, 7.1, 1.1 Hz, 1H), 4.58 (t, J=6.5 Hz, 2H), 3.64 (t, J=6.5 Hz, 2H), 3.59 (s, 3H).

Compound I-11: ¹H NMR (500 MHz, DMSO-dr) δ 9.68 (s, 1H), 9.11 (s, 1H), 8.58 (s, 1H), 8.08 (s, 1H), 7.91 (d, J=7.9 Hz, 1H), 7.67 (s, 1H), 7.58-7.53 (m, 2H), 7.48-7.42 (m, 1H), 6.38 (tt, J=54.7, 3.8 Hz, 1H), 4.64 (td, J=15.2, 3.7 Hz, 2H), 3.59 (s, 3H).

Compound I-12: ¹H NMR (500 MHz, DMSO-d₆) δ 10.03 (s, 1H), 8.99-8.95 (m, 1H), 8.88 (s, 1H), 8.60 (s, 1H), 8.12 (d, J=8.1 Hz, 1H), 7.90 (d, J=7.7 Hz, 1H), 7.55 (s, 1H), 7.51-7.46 (m, 1H), 7.46-7.41 (m, 1H), 7.18 (d, J=1.7 Hz, 1H), 7.15 (dd, J=8.1, 1.7 Hz, 1H), 3.91 (s, 3H), 3.60 (s, 3H), 3.49 (s, 2H), 3.34 (s, 1H), 3.19-3.06 (m, 2H), 2.85 (s, 3H).

Compound I-13: ¹H NMR (500 MHz, DMSO-d₆) δ 9.91 (s, 1H), 9.09 (s, 1H), 8.49 (s, 1H), 8.43 (s, 1H), 7.86 (d, J=8.0 Hz, 1H), 7.52 (d, J=8.8 Hz, 1H), 7.49 (s, 1H), 7.42 (dd, J=8.8, 2.7 Hz, 1H), 7.39-7.34 (m, 2H), 7.27 (t, J=7.7 Hz, 1H), 4.03 (d, J=13.0 Hz, 2H), 3.62-3.54 (m, 5H), 3.24 (q, J=9.6, 9.1 Hz, 2H), 3.09 (t, J=12.2 Hz, 2H), 2.91 (s, 3H).

Compound I-14: ¹H NMR (500 MHz, DMSO-d₆) 9.70 (s, 1H), 9.60 (s, 1H), 9.08 (d, J=8.2 Hz, 1H), 8.57 (s, 1H), 7.90 (d, J=7.9 Hz, 1H), 7.65 (d, J=8.9 Hz, 2H), 7.55-7.49 (m, 2H), 7.47-7.39 (m, 1H), 7.06 (d, J=9.0 Hz, 2H), 3.81 (d, J=13.0 Hz, 2H), 3.59 (s, 5H), 3.21 (dd, J=9.9, 9.4 Hz, 2H), 2.95 (t, J=12.1 Hz, 2H), 2.89 (s, 3H).

Compound I-15: ¹H NMR (500 MHz, DMSO-d₆) δ 9.52 (s, 1H), 8.75 (s, 1H), 8.66 (s, 1H), 8.50 (s, 1H), 7.87 (dd, J=6.5, 2.2 Hz, 1H), 7.54 (d, J=8.6 Hz, 1H), 7.50 (s, 1H), 7.42-7.35 (m, 2H), 6.80 (d, J=2.5 Hz, 1H), 6.66 (dd, J=8.6, 2.5 Hz, 1H), 3.93 (d, J=13.2 Hz, 2H), 3.79 (s, 3H), 3.63 (d, J=11.6 Hz, 3H), 3.57 (s, 3H), 3.25 (dt, J=12.5, 6.2 Hz, 2H), 3.21-3.13 (m, 2H), 3.02 (t, J=11.7 Hz, 2H), 1.29 (t, J=7.3 Hz, 3H).

Compound I-16: ¹H NMR (500 MHz, DMSO-d₆) δ 9.60 (s, 1H), 9.52 (s, 1H), 9.08 (d, J=8.2 Hz, 1H), 8.57 (s, 1H), 7.90 (d, J=7.9 Hz, 1H), 7.65 (d, J=8.9 Hz, 2H), 7.56-7.48 (m, 2H), 7.47-7.41 (m, 1H), 7.07 (d, J=9.0 Hz, 2H), 3.82 (d, J=13.2 Hz, 4H), 3.59 (s, 5H), 3.23 (dt, J=12.7, 6.3 Hz, 2H), 3.19-3.11 (m, 2H), 2.96 (t, J=11.7 Hz, 2H), 1.28 (t, J=7.3 Hz, 3H).

Compound I-17: ¹H NMR (500 MHz, DMSO-d₆) δ 8.77 (s, 1H), 8.65 (s, 1H), 8.50 (s, 1H), 7.87 (dd, J=6.5, 2.2 Hz, 1H), 7.61-7.47 (m, 2H), 7.45-7.30 (m, 2H), 6.80 (s, 1H), 6.73-6.60 (m, 1H), 3.88 (d, J=11.8 Hz, 2H), 3.79 (s, 3H), 3.57 (s, 3H), 2.81 (br, 6H), 2.07 (d, J=8.0 Hz, 2H), 1.79-1.65 (m, 2H).

Compound I-22: ¹H NMR (500 MHz, DMSO-d₆) δ 9.69 (s, 1H), 9.01 (d, J=5.4 Hz, 1H), 8.56 (s, 1H), 8.52 (s, 1H), 8.07 (d, J=7.5 Hz, 1H), 7.89 (d, J=7.9 Hz, 1H), 7.53 (d, J=7.3 Hz, 2H), 7.48-7.41 (m, 1H), 7.13 (d, J=8.8 Hz, 1H), 3.80-3.73 (m, 4H), 3.58 (s, 3H), 3.53-3.45 (m, 4H).

Compound I-23: ¹H NMR (500 MHz, DMSO-d₆) δ 9.68 (s, 1H), 9.03 (s, 1H), 8.56 (s, 1H), 8.50 (s, 1H), 8.04 (d, J=8.3 Hz, 1H), 7.91 (d, J=7.9 Hz, 1H), 7.55 (s, 1H), 7.52 (t, J=7.7 Hz, 1H), 7.45 (t, J=7.4 Hz, 1H), 7.17 (d, J=8.0 Hz, 1H), 4.34 (d, J=12.5 Hz, 2H), 3.59 (s, 3H), 2.94 (t, J=12.3 Hz, 2H), 2.81 (s, 3H), 2.54 (s, 3H), 2.04 (d, J=10.2 Hz, 2H), 1.69-1.48 (m, 2H).

Compound I-25: ¹H NMR (500 MHz, DMSO-d₆) δ 10.07 (s, 1H), 9.56 (s, 1H), 9.07 (d, J=8.3 Hz, 1H), 8.64 (s, 1H), 8.26 (d, J=2.4 Hz, 1H), 8.00 (dd, J=8.7, 2.0 Hz, 1H), 7.91 (d, J=7.9 Hz, 1H), 7.60 (d, J=8.8 Hz, 1H), 7.56 (s, 1H), 7.55-7.49 (m, 1H), 7.48-7.43 (m, 1H), 3.60 (s, 5H), 3.31-3.22 (m, 2H), 3.21-3.04 (m, 6H), 1.27 (t, J=7.3 Hz, 3H).

Compound I-26: ¹H NMR (500 MHz, DMSO-d₆) δ 9.76 (s, 1H), 9.60 (s, 1H), 9.09 (d, J=8.1 Hz, 1H), 8.63 (s, 1H), 7.90 (d, J=7.9 Hz, 1H), 7.65 (d, 1H), 7.53 (s, 1H), 7.51 (d, J=8.2 Hz, 1H), 7.44 (t, J=7.8 Hz, 1H), 7.10-7.01 (m, 2H), 4.24 (q, J=6.9 Hz, 1H), 3.81 (d, J=12.9 Hz, 2H), 3.55 (d, J=11.8 Hz, 2H), 3.21 (q, J=9.5 Hz, 2H), 2.95 (t, J=12.0 Hz, 2H), 2.89 (s, 3H), 1.27 (t, J=7.1 Hz, 3H).

Compound I-27: ¹H NMR (500 MHz, DMSO-d₆) δ 10.07 (s, 1H), 9.82 (s, 1H), 9.08 (d, J=8.3 Hz, 1H), 8.71 (s, 1H), 8.27 (d, J=2.4 Hz, 1H), 7.99 (dd, J=8.7, 2.0 Hz, 1H), 7.91 (d, J=7.9 Hz, 1H), 7.60 (d, J=8.7 Hz, 1H), 7.56 (s, 1H), 7.52 (t, J=7.7 Hz, 1H), 7.49-7.42 (m, 1H), 4.26 (q, J=7.0 Hz, 2H), 3.53 (d, J=9.2 Hz, 2H), 3.14 (dd, J=18.9, 8.9 Hz, 6H), 2.91 (s, 3H), 1.28 (t, J=7.1 Hz, 3H).

Example 3: Biological Activities of Compounds of the Present Application

Biological activities of compounds of the present application to modulate various kinases, including NEKs, were assessed. As presented in Table 2, compounds of the present application potently modulates NEKs.

TABLE 2

| Cmpd | NEK2 | NEK6 | NEK7 | NEK9 | SLK | GSK3B | MERTK | AXL | GRK4 | DRAK1 | RSK1 | CLK | DMPK |
|---|---|---|---|---|---|---|---|---|---|---|---|---|---|
| I-7  | A  | C | B | AA |   | B | B | B |   |   | B | A |   |
| I-1  | AA | A | B | AA | A | B | B | A | C | A | A | A | A |
| I-4  | A  | C | C | B  | C | D | D | D |   | C | B | A | B |
| I-3  | A  | A | A | A  | C | C | D | D |   | A | B | C | D |
| I-5  | A  | D | C | A  | B | D | C | C |   | B | C | C | D |
| I-2  | A  | B | A | A  | C | C | D | D |   | A | C | B | D |
| I-9  | A  | B | B | AA |   |   |   |   |   |   |   | B | C |
| I-6  | AA | B | A | A  | C | D | D | C |   | B | A | A | B |
| I-10 | A  | D | C | A  |   |   |   |   |   |   |   | C | B |
| I-11 | B  | D | C | A  |   |   |   |   |   |   |   | D | C |
| I-12 | A  | C | C | C  |   |   |   |   |   |   |   | B | C |
| I-13 | A  | C | B | C  |   |   |   |   |   |   |   | D | D |
| I-14 | A  | C | A | AA |   |   |   |   |   |   |   | D | B |
| I-15 | AA | B | B | A  |   |   |   |   |   |   |   | B | B |
| I-16 | AA | B | B | AA |   |   |   |   |   |   |   | A | A |
| I-17 | AA | B |   | AA | A |   |   |   |   |   |   | A | A |

TABLE 2-continued

| Cmpd | NEK2 | NEK6 | NEK7 | NEK9 | SLK | GSK3B | MERTK | AXL | GRK4 | DRAK1 | RSK1 | CLK | DMPK |
|---|---|---|---|---|---|---|---|---|---|---|---|---|---|
| I-18 | A | B | B | B | | | | | | | | D | D |
| I-19 | D | C | B | D | | | | | | | | D | D |
| I-20 | A | B | A | A | | | | | | | | C | C |
| I-21 | AA | B | B | A | | | | | | | | B | B |
| I-22 | A | C | B | A | | | | | | | | B | B |
| I-23 | AA | B | B | AA | | | | | | | | A | A |
| I-25 | AA | | | A | | | | | | | | | |
| I-26 | A | | | A | | | | | | | | | |
| I-27 | B | | | B | | | | | | | | | |
| I-28 | A | | | AA | | | | | | | | | |
| I-29 | AA | | | AA | | | | | | | | | |
| I-30 | B | | | A | | | | | | | | | |
| I-31 | A | | | A | | | | | | | | | |
| I-32 | A | | | A | | | | | | | | | |
| I-33 | C | | | B | | | | | | | | | |

AA: $IC_{50} \leq 50$ nM, A: 50 nM $< IC_{50} \leq 250$ nM, B: 250 nM $< IC_{50} \leq 1000$ nM, C: 1000 nM $< IC_{50} \leq 5000$ nM, D: $IC_{50} \geq 5000$ nM.

The invention claimed is:

1. A compound of Formula I:

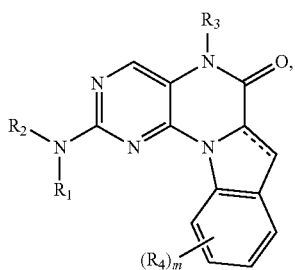

(I)

or a pharmaceutically acceptable salt thereof, wherein:
═══ represents a single or double bond;
$R_1$ is $C_6$-$C_{10}$ aryl or heteroaryl having one or two 5- or 6-membered rings and 1-4 heteroatoms selected from N, O, and S, wherein the aryl or heteroaryl is substituted with one or two $R_{S1}$;
each $R_{S1}$ independently is $C_1$-$C_6$ alkyl, $C_1$-$C_6$ haloalkyl, halogen, cyano, $OR_a$, $NR_aR_b$, $C(O)NR_aR_b$, $S(O)_2NR_aR_b$, or L-$T_1$, wherein at least one $R_{S1}$ is $C_1$-$C_6$ haloalkyl, $S(O)_2NR_aR_b$, or L-$T_1$;
L is a bond, —C(O)—, —S(O)$_n$—, —S(O)$_n$NH—, —C(O)NH—, or —(CH$_2$)$_p$—;
$T_1$ is $C_3$-$C_8$ cycloalkyl or heterocyclyl having one 5- or 6-membered ring and 1-4 heteroatoms selected from N, O, and S, wherein the cycloalkyl or heterocyclyl is optionally substituted with one or two $X_1$;
each $X_1$ independently is $C_1$-$C_6$ alkyl, $C_1$-$C_6$ haloalkyl, halogen, cyano, $C_3$-$C_8$ cycloalkyl, $C_6$-$C_{10}$ aryl, heterocyclyl having one or two 5- or 6-membered rings and 1-4 heteroatoms selected from N, O, and S, heteroaryl having one or two 5- or 6-membered rings and 1-4 heteroatoms selected from N, O, and S, $OR_a$, $NR_aR_b$, $C(O)OR_a$, $C(O)NR_aR_b$, $S(O)_nOR_a$, or $S(O)_nNR_aR_b$, wherein the cycloalkyl, aryl, heterocyclyl, or heteroaryl is optionally substituted with one or two $R_{S2}$;
each $R_{S2}$ independently is $C_1$-$C_6$ alkyl, $C_1$-$C_6$ haloalkyl, halogen, cyano, $OR_a$, or $NR_aR_b$;
$R_2$ is H or $C_1$-$C_6$ alkyl;
$R_3$ is $C_1$-$C_6$ alkyl;
each $R_4$ independently is $C_1$-$C_6$ alkyl, $C_1$-$C_6$ haloalkyl, halogen, cyano, $OR_a$, or $NR_aR_b$;
each $R_a$ and each $R_b$ independently is H or $C_1$-$C_6$ alkyl;

m is 0, 1, 2, 3, or 4;
each n independently is 0, 1, or 2; and
p is 1, 2, 3, 4, 5, or 6.

2. The compound of claim 1, of Formula Ia1:

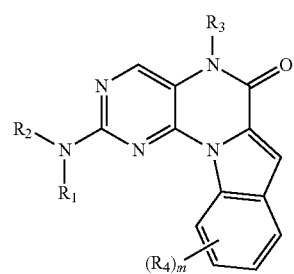

(Ia1)

or a pharmaceutically acceptable salt thereof.

3. The compound of claim 1, wherein $R_1$ is $C_6$-$C_{10}$ aryl substituted with one or two $R_{S1}$.

4. The compound of claim 1, wherein $R_1$ is heteroaryl having one or two 5- or 6-membered rings and 1-4 heteroatoms selected from N, O, and S, substituted with one or two $R_{S1}$.

5. The compound of claim 1, wherein each $R_{S1}$ independently is $C_1$-$C_6$ alkyl, $C_1$-$C_6$ haloalkyl, halogen, cyano, $OR_a$, $NR_aR_b$, $C(O)NR_aR_b$, $S(O)_2NR_aR_b$, or L-$T_1$, wherein at least one $R_{S1}$ is L-$T_1$.

6. The compound of claim 1, wherein one $R_{S1}$ is L-$T_1$; and at least one $R_{S1}$ is $C_1$-$C_6$ alkyl, $C_1$-$C_6$ haloalkyl, halogen, cyano, $OR_a$, $NR_aR_b$, $C(O)NR_aR_b$, or $S(O)_2NR_aR_b$.

7. The compound of claim 1, wherein two $R_{S1}$ are L-$T_1$.

8. The compound of claim 1, wherein one $R_{S1}$ is $C_1$-$C_6$ haloalkyl or $S(O)_2NR_aR_b$.

9. The compound of claim 1, wherein L is a bond, —C(O)—, or —(CH$_2$)$_p$—.

10. The compound of claim 1, wherein $T_1$ is heterocyclyl having one 5- or 6-membered ring and 1-4 heteroatoms selected from N, O, and S, optionally substituted with one or more $X_1$.

11. The compound of claim 1, wherein each $X_1$ independently is $C_1$-$C_6$ alkyl, $C_1$-$C_6$ haloalkyl, halogen, cyano, $C_3$-$C_8$ cycloalkyl, or heterocyclyl having one or two 5- or 6-membered rings and 1-4 heteroatoms selected from N, O, and S, $OR_a$, $NR_aR_b$, $C(O)OR_a$, $C(O)NR_aR_b$, $S(O)_nOR_a$, or $S(O)_nNR_aR_b$, wherein the cycloalkyl or heterocyclyl is optionally substituted with one or more $R_{S2}$.

12. The compound of claim 1, wherein each $X_1$ independently is $C_1$-$C_6$ alkyl, $C_1$-$C_6$ haloalkyl, halogen, cyano, $C_3$-$C_8$ cycloalkyl, heterocyclyl having one 6-membered ring and 1-4 heteroatoms selected from N, O, and S, $OR_a$, or $C(O)NR_aR_b$.

13. The compound of claim 1, wherein each $R_{S2}$ independently is $C_1$-$C_6$ alkyl, $C_1$-$C_6$ haloalkyl, or halogen.

14. The compound of claim 1, wherein $R_2$ is H.

15. The compound of claim 1, wherein $R_3$ is $C_1$-$C_3$ alkyl.

16. The compound of claim 1, wherein m is 0.

17. The compound of claim 1, of Formula Ib or Ib1:

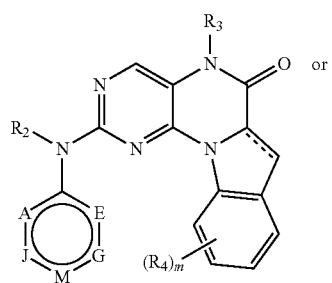

(Ib)

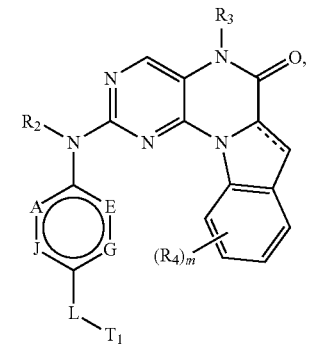

(Ib1)

or a pharmaceutically acceptable salt thereof, wherein A, E, G, J, and M are each independently CH, $CR_{S1}$, or N.

18. The compound of claim 1, of Formula Ic or Ic1:

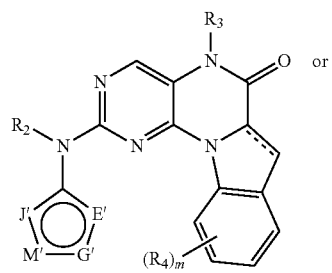

(Ic)

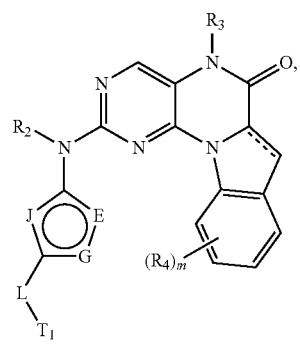

(Ic1)

or a pharmaceutically acceptable salt thereof, wherein E', G', J', and M' are each independently CH, $CR_{S1}$, $NR_{S1}$, or N.

19. The compound of claim 1, of any of Formulae Id1-Id8:

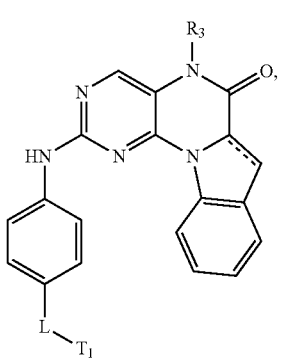

(Id1)

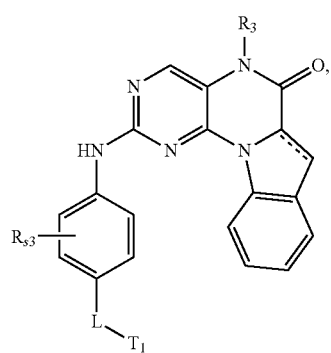

(Id2)

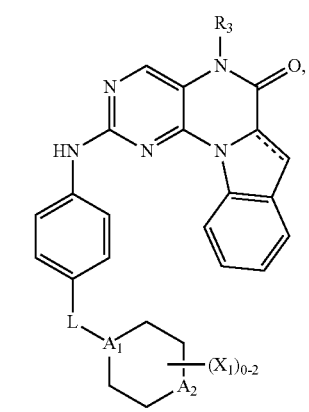

(Id3)

(Id4)
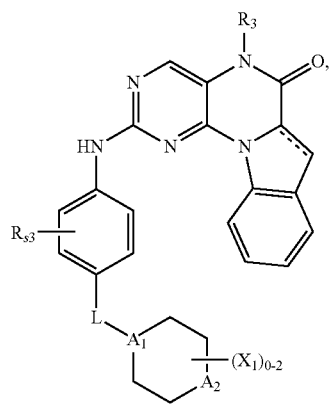
(Id5)
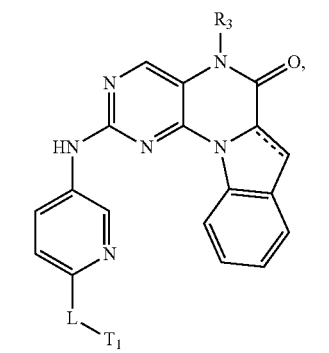
(Id6)
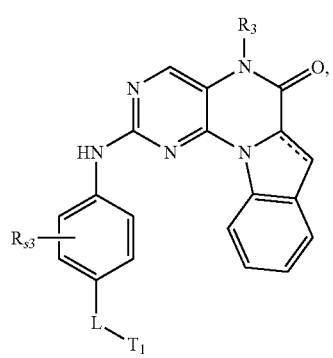
(Id7)
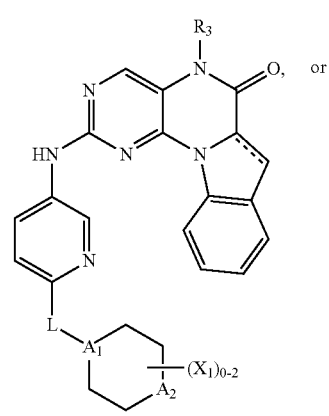
(Id8)
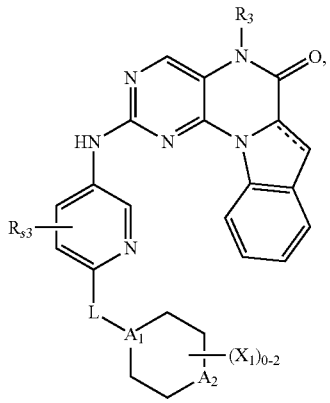
or a pharmaceutically acceptable salt thereof, wherein:
$A_1$ is CH or N;
$A_2$ is $CH_2$, $CHX_1$, NH, $NX_1$, or O; and
$R_{S3}$ is $C_1$-$C_6$ alkyl, $C_1$-$C_6$ haloalkyl, halogen, cyano, $OR_a$, $NR_aR_b$, $C(O)NR_aR_b$, or $S(O)_2NR_aR_b$.
20. The compound of claim 1, selected from
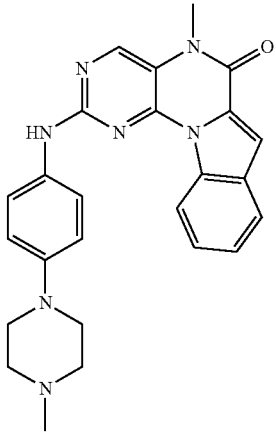 [SMILES: CN1CCN(c2ccc(Nc3ncc4c(n3)n3c(cc5ccccc53)c(=O)n4C)cc2)CC1]
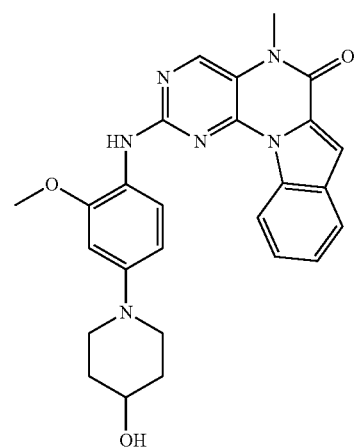 [SMILES: COc1cc(N2CCC(O)CC2)ccc1Nc1ncc2c(n1)n1c(cc3ccccc31)c(=O)n2C]

55
-continued
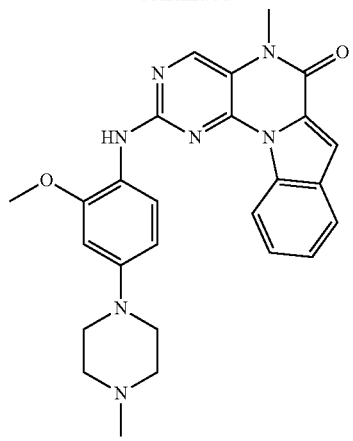 [SMILES: COc1cc(N2CCN(C)CC2)ccc1Nc1ncc2c(n1)n1c(cc3ccccc31)c(=O)n2C]
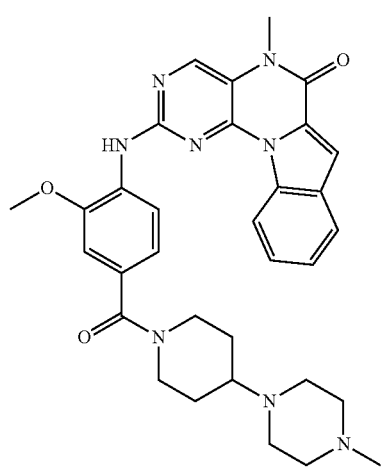
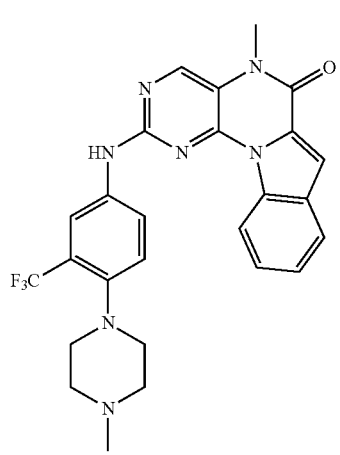 [SMILES: CN1CCN(c2ccc(Nc3ncc4c(n3)n3c(cc5ccccc53)c(=O)n4C)cc2C(F)(F)F)CC1]
56
-continued
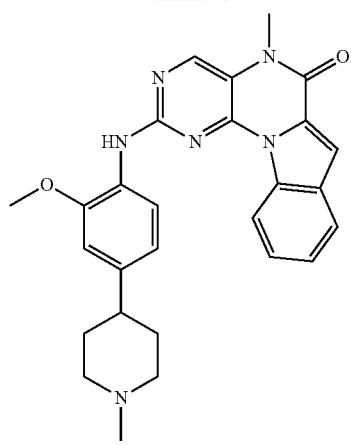 [SMILES: COc1cc(C2CCN(C)CC2)ccc1Nc1ncc2c(n1)n1c(cc3ccccc31)c(=O)n2C]
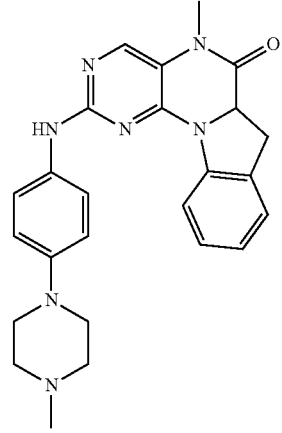 [SMILES: CN1CCN(c2ccc(Nc3ncc4c(n3)N3c5ccccc5CC3C(=O)N4C)cc2)CC1]
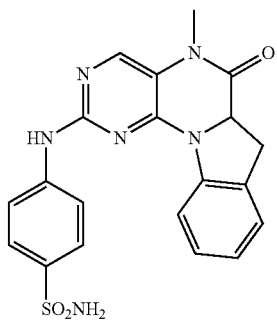 [SMILES: CN1C(=O)C2Cc3ccccc3N2c2nc(Nc3ccc(S(N)(=O)=O)cc3)ncc21]

57
-continued
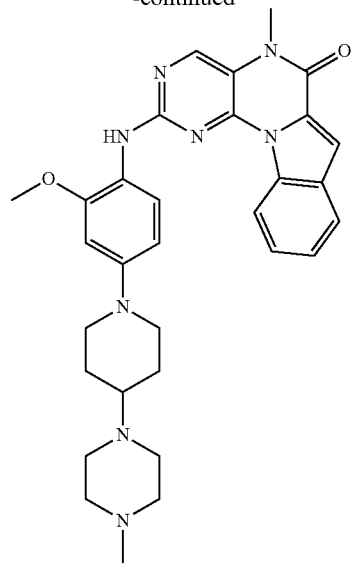
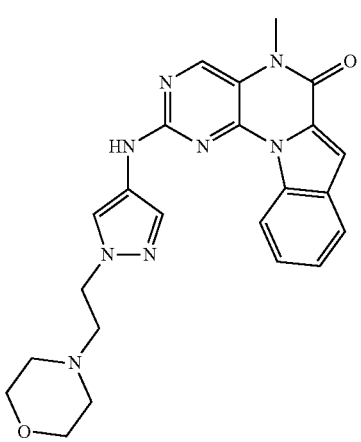
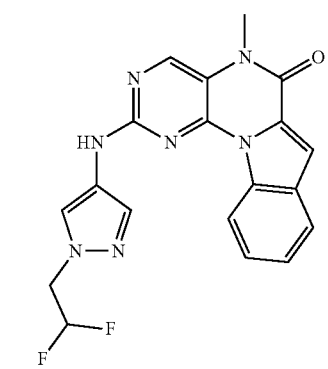
58
-continued
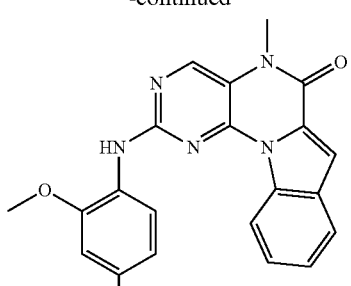
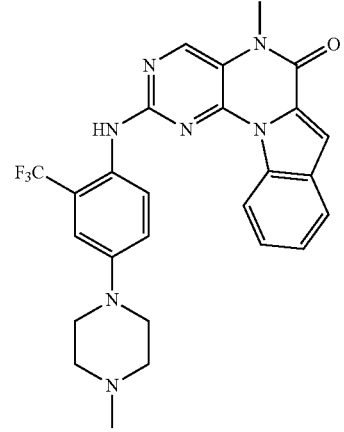 [SMILES: CN1CCN(c2ccc(Nc3ncc4c(n3)n3c(cc5ccccc53)c(=O)n4C)c(C(F)(F)F)c2)CC1]
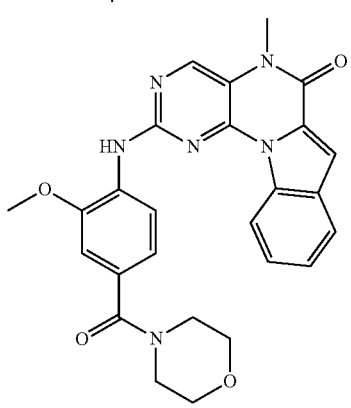
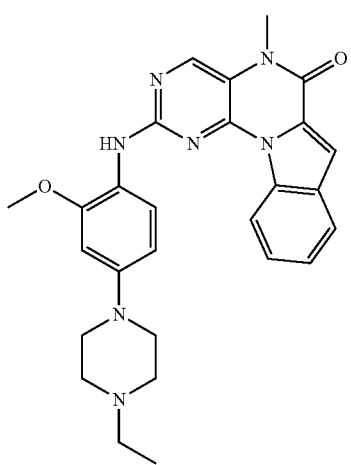 [SMILES: CCN1CCN(c2ccc(Nc3ncc4c(n3)n3c(cc5ccccc53)c(=O)n4C)c(OC)c2)CC1]

-continued
59
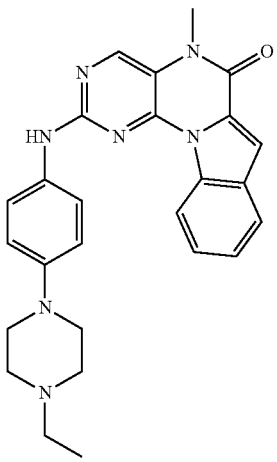 [SMILES: CCN1CCN(c2ccc(Nc3ncc4c(n3)n3c(cc5ccccc53)c(=O)n4C)cc2)CC1]
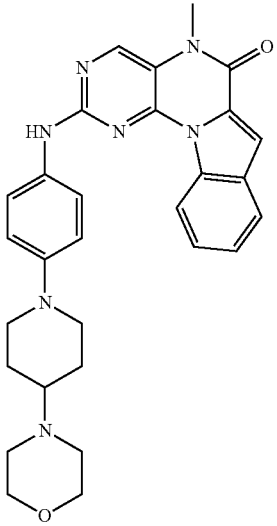 [SMILES: Cn1c(=O)c2cc3ccccc3n2c2nc(Nc3ccc(N4CCC(N5CCOCC5)CC4)cc3)ncc21]
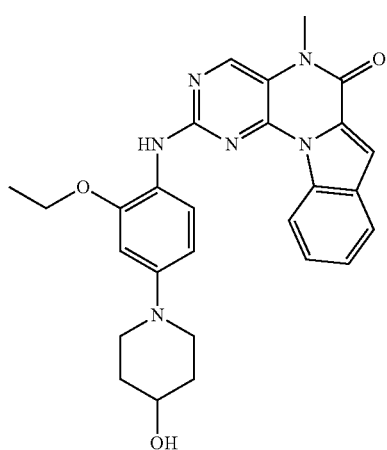 [SMILES: CCOc1cc(N2CCC(O)CC2)ccc1Nc1ncc2c(n1)n1c(cc3ccccc31)c(=O)n2C]
-continued
60
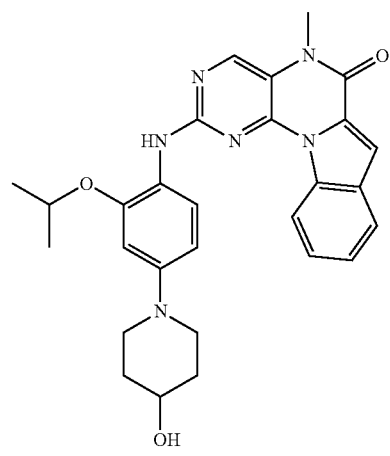 [SMILES: CC(C)Oc1cc(N2CCC(O)CC2)ccc1Nc1ncc2c(n1)n1c(cc3ccccc31)c(=O)n2C]
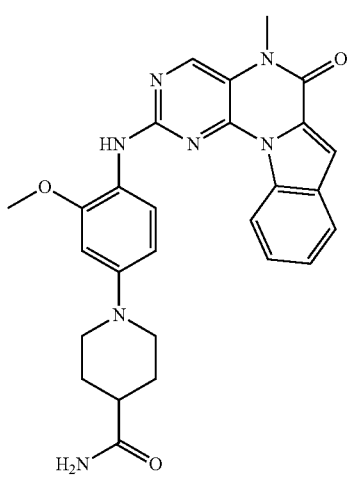 [SMILES: COc1cc(N2CCC(C(N)=O)CC2)ccc1Nc1ncc2c(n1)n1c(cc3ccccc31)c(=O)n2C]
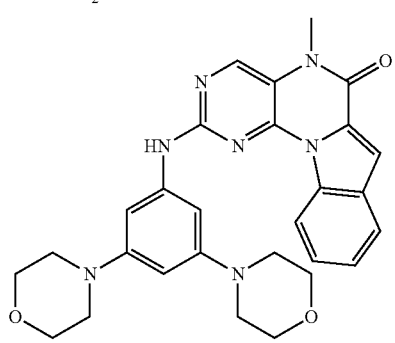
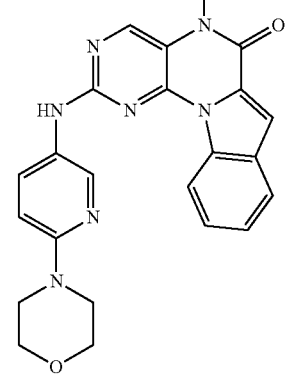

61
-continued
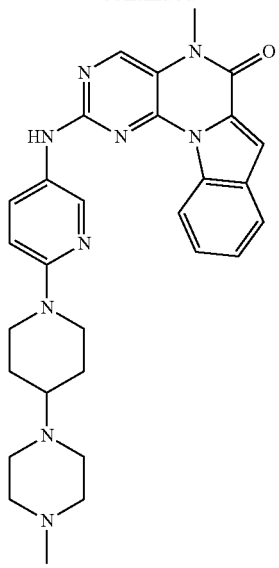 [SMILES: CN1CCN(C2CCN(c3ccc(Nc4ncc5c(n4)n4c(cc6ccccc64)c(=O)n5C)cn3)CC2)CC1]
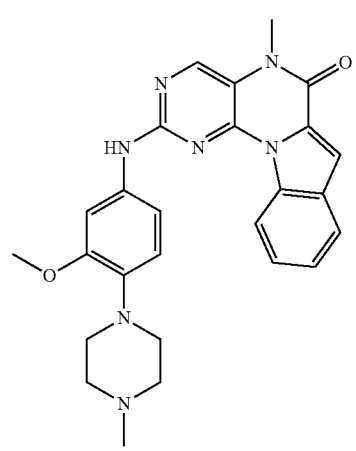 [SMILES: COc1cc(Nc2ncc3c(n2)n2c(cc4ccccc42)c(=O)n3C)ccc1N1CCN(C)CC1]
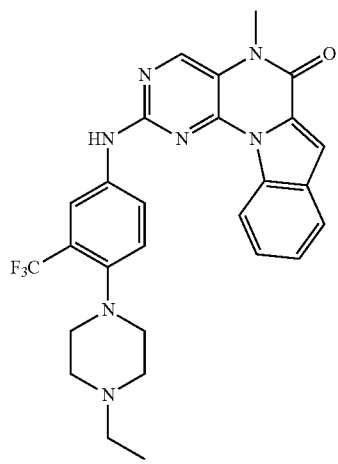
62
-continued
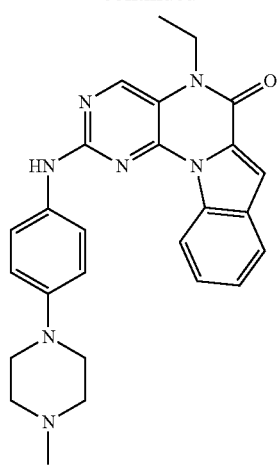 [SMILES: CCn1c(=O)c2cc3ccccc3n2c2nc(Nc3ccc(N4CCN(C)CC4)cc3)ncc21]
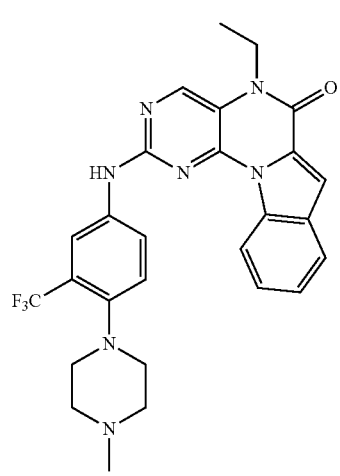 [SMILES: CCn1c(=O)c2cc3ccccc3n2c2nc(Nc3ccc(N4CCN(C)CC4)c(C(F)(F)F)c3)ncc21]
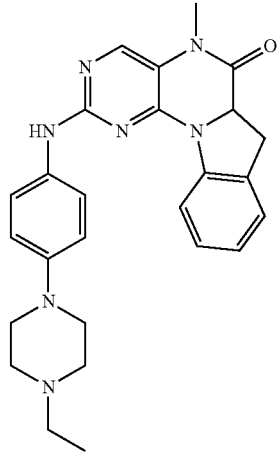 [SMILES: CCN1CCN(c2ccc(Nc3ncc4c(n3)N3c5ccccc5CC3C(=O)N4C)cc2)CC1]

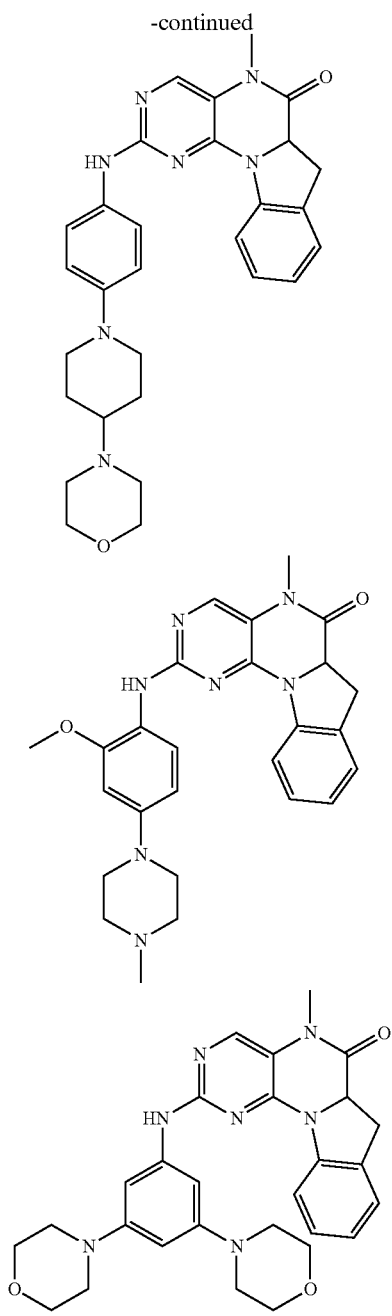

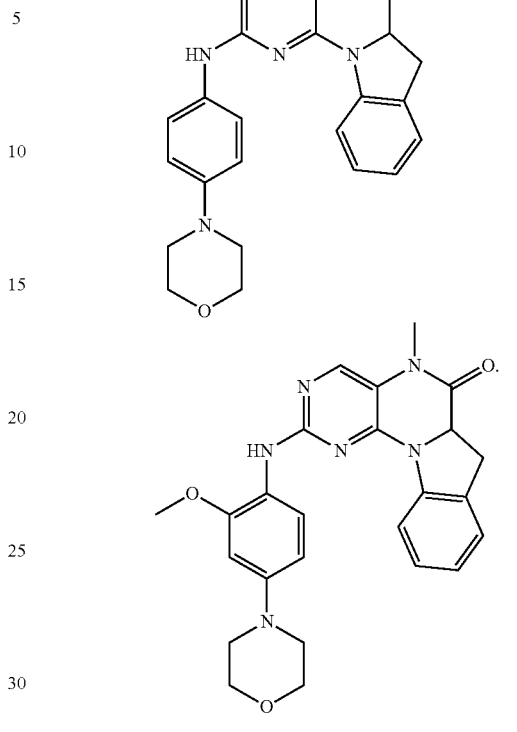

21. A pharmaceutical composition comprising a therapeutically effective amount of a compound of claim 1 or a pharmaceutically acceptable salt thereof, and a pharmaceutically acceptable carrier.

22. A method of treating cancer in a subject, wherein the cell of the cancer comprises an activated NEK or wherein the subject is identified as being in need of inhibition of NEK for the treatment or prevention of cancer, comprising administering to the subject a therapeutically effective amount of a compound of claim 1 or a pharmaceutically acceptable salt thereof.

23. A method of modulating NEK, comprising administering to a subject in need thereof a therapeutically effective amount of a compound of claim 1 or a pharmaceutically acceptable salt thereof.

* * * * *

UNITED STATES PATENT AND TRADEMARK OFFICE
CERTIFICATE OF CORRECTION

PATENT NO. : 11,279,707 B2
APPLICATION NO. : 16/956048
DATED : March 22, 2022
INVENTOR(S) : Nathanael S. Gray Page 1 of 1

It is certified that error appears in the above-identified patent and that said Letters Patent is hereby corrected as shown below:

In the Claims

Claim 19, Column 53, Lines 37-50, should read:

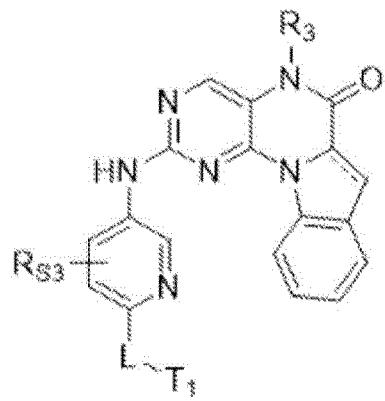

Signed and Sealed this
Sixteenth Day of August, 2022

Katherine Kelly Vidal
Director of the United States Patent and Trademark Office